US012778122B2

(12) United States Patent
Lee et al.

(10) Patent No.: US 12,778,122 B2
(45) Date of Patent: *Nov. 3, 2026

(54) ANTIBACTERIAL COMPOSITION

(71) Applicant: LG CHEM, LTD., Seoul (KR)

(72) Inventors: Ji Seok Lee, Daejeon (KR); Soonhee Kang, Daejeon (KR); Sanggon Kim, Daejeon (KR); Leehyeon Baek, Daejeon (KR); Haesung Yun, Daejeon (KR); Hwanhee Lee, Daejeon (KR); Da Sol Chung, Daejeon (KR); Seonjung Jung, Daejeon (KR); Hyungsam Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 561 days.

This patent is subject to a terminal disclaimer.

(21) Appl. No.: 18/027,430

(22) PCT Filed: Jun. 29, 2022

(86) PCT No.: PCT/KR2022/009358

§ 371 (c)(1),
(2) Date: Mar. 21, 2023

(87) PCT Pub. No.: WO2023/287071

PCT Pub. Date: Jan. 19, 2023

(65) Prior Publication Data

US 2024/0107999 A1 Apr. 4, 2024

(30) Foreign Application Priority Data

Jul. 16, 2021 (KR) ........................ 10-2021-0093569

(51) Int. Cl.

*A01N 37/44* (2006.01)
*A01N 25/04* (2006.01)
*A01N 33/12* (2006.01)
*A01P 1/00* (2006.01)
*C12Q 1/18* (2006.01)

(52) U.S. Cl.

CPC ............. *A01N 37/44* (2013.01); *A01N 25/04* (2013.01); *A01N 33/12* (2013.01); *A01P 1/00* (2021.08); *C12Q 1/18* (2013.01)

(58) Field of Classification Search

None
See application file for complete search history.

(56) References Cited

U.S. PATENT DOCUMENTS

2003/0191264 A1 10/2003 Crass et al.
2005/0095266 A1 5/2005 Perichaud et al.
2005/0164903 A1 7/2005 Ko et al.
2010/0178427 A1 7/2010 Deisenroth et al.
2011/0076387 A1 3/2011 Koehl et al.
2013/0183456 A1 7/2013 Kim
2013/0209536 A1 8/2013 Krogman et al.
2016/0361698 A1 12/2016 Yanagisawa et al.
2018/0362462 A1 12/2018 Monteiro et al.
2019/0194286 A1 6/2019 Yokoyama et al.
2023/0120607 A1* 4/2023 Lee ...................... C09D 133/14 525/57
2024/0107999 A1 4/2024 Lee et al.
2024/0108001 A1* 4/2024 Kang ..................... A01N 37/44

FOREIGN PATENT DOCUMENTS

CN 105155269 A 12/2015
CN 109135232 A 1/2019
EP 0537774 A1 4/1993
JP H05-086575 4/1993
JP 2000045179 A 2/2000
JP 2000-154105 6/2000
JP 3357094 12/2002
JP 2003-306404 A 10/2003
JP 2004-511582 A 4/2004
JP 2004-346291 A 12/2004
JP 2005-508400 A 3/2005
JP 2006-507111 A 3/2006
JP 2010-531156 A 9/2010
(Continued)

OTHER PUBLICATIONS

Ping. Journal of Membrane Science, 2019, 570-571, 286-293 (Year: 2019).*
Wang. Dental Materials, 2017, 33, 1127-1138 (Year: 2017).*
CAS Registry Nos. 1481646-07-4, 1384055-71-3, 1384055-69-9, 1346411-03-7, 1346221-69-9, 1346106-10-2, 1345977-96-9, 1303644-49-6, 1303644-46-3, 1294040-50-8, 1293911-72-4, 1268498-75-4, 1226982-43-9, 1190428-10-4, 1190428-07-9, 1189369-22-2, 944471-53-8, 756814-00-3, 738556-93-9, 736107-13-4, 194874-78-7, 123913-36-0, and 123913-35-9, Database Registry [online], entered STN: from 1989 to 2013; retrieved from: STN, pp. 1-23.
Nakatsuji, "Structure and Surface Properties of Gemini Surfactants," Journal of the Adhesion Society of Japan vol. 40 No. 10 (2004), Aug. 13, 2004, pp. (25)-(29), [441]-[445].
Lin et al. "Effect of alkyl chain length and fluorine content on the surface characteristics and antibacterial activity of surfaces grafted with brushes containing quaternized ammonium and fluoro-containing monomers," Colloids and Surfaces B: Biointerfaces vol. 202, Jun. 2021, 111674.
Mohammed et al., "Antibacterial Activity of Quaternary Ammonium Salt from Diethylaminoethyl Methacrylate," E-Journal of Chemistry, 7(S1):S61-S66 (2010).
(Continued)

*Primary Examiner* — Noble E Jarrell
(74) *Attorney, Agent, or Firm* — Bryan Cave Leighton Paisner LLP

(57) ABSTRACT

Provided is an antibacterial composition comprising at least one compound including a quaternary ammonium structure having an acrylate group or a methacrylate group, and having an antibacterial strength A of 90% or more against at least one strain selected from Gram-positive bacteria and Gram-negative bacteria, and an acute oral toxicity dose LD50 of 300 mg/Kg or more, where the antibacterial strength A equals $(1-A_{sample}/A_{Reference})\times 100$, where $A_{sample}$ equals an absorbance of an inoculated medium solution incubated with the antibacterial composition, and $A_{Reference}$ equals an absorbance of an inoculated medium solution incubated without addition of the antibacterial composition.

20 Claims, 4 Drawing Sheets

(56) References Cited

FOREIGN PATENT DOCUMENTS

| | | | | | |
|---|---|---|---|---|---|
| JP | 2012-208169 | | | 10/2012 | |
| JP | 2013-505973 | A | | 2/2013 | |
| JP | 2013-542332 | | | 11/2013 | |
| JP | 5523948 | | | 6/2014 | |
| JP | 2017202982 | A | | 11/2017 | |
| JP | 2021-011578 | | | 2/2021 | |
| JP | 6866272 | | | 4/2021 | |
| JP | 2024502922 | A | | 1/2024 | |
| JP | 2024505838 | A | | 2/2024 | |
| KR | 10-1285301 | | | 7/2013 | |
| WO | 2012072218 | A1 | | 6/2012 | |
| WO | 2013117284 | A1 | | 8/2013 | |
| WO | 2014-003095 | | | 1/2014 | |
| WO | 2015-133455 | A | | 11/2015 | |
| WO | 2016182444 | A1 | | 11/2016 | |
| WO | 2017022696 | A1 | | 2/2017 | |
| WO | 2017057571 | A1 | | 4/2017 | |
| WO | WO-2022075763 | A1 | * | 4/2022 | ........... C09D 129/04 |

OTHER PUBLICATIONS

Daoudi et al., "Synthesis, Characterizationand Antibacterial Activity of Quaternary Ammonium Compounds Bearing Mixed N-Substituted Groups," Chemical Science Transactions, 3(1):281-291 (2014).

Mancuso et al., "Synthesis and Antibacterial Activity of Polymerizable Acryloyloxyalkyltriethyl Ammonium Salts," ChemPlusChem, 82:1235-1244 (2017).

* cited by examiner monomer 3
4,2,4,12

ANTIBACTERIAL COMPOSITION

CROSS-REFERENCE TO RELATED APPLICATION(S)

This application is a National Stage Application of International Application No. PCT/KR2022/009358 filed on Jun. 29, 2022, which claims priority to and the benefit of Korean Patent Application No. 10-2021-0093569 filed in the Korean Intellectual Property Office on Jul. 16, 2021, the entire contents of which are incorporated herein by reference.

TECHNICAL FIELD

The present invention relates to an antibacterial composition.

BACKGROUND ART

Recently, various products such as daily supplies or hygiene products are required to have antibacterial properties.

The degree of antibacterial properties required and the material requirements for imparting antibacterial properties differ depending on the material of the product requiring antibacterial properties and the state of final use. For example, the properties of the material for imparting antibacterial properties and the degree of antibacterial properties vary depending on the amount of antibacterial material applied to a product and the materials used together.

Therefore, there is a need for developing an antibacterial material suitable for application to each of various products.

DETAILED DESCRIPTION OF THE INVENTION

Technical Problem

The present invention has been made in an effort to provide an antibacterial composition comprising an antibacterial material which has hydrophilicity and hydrophobicity, and thus, is advantageous for imparting antibacterial properties, and is capable of not only imparting antibacterial properties but also solving safety problems due to the leakage of antibacterial materials, by forming a copolymer with an acryl-based resin and the like.

Technical Solution

An exemplary embodiment of the present invention provides an antibacterial composition comprising at least one compound comprising a quaternary ammonium structure having an acrylate group or methacrylate group, and having an antibacterial strength A of 90% or more which is measured by the following Method 1 for at least one strain of Gram-positive bacteria and Gram-negative bacteria and an acute oral toxicity dose LD50 of 300 mg/Kg or more.

[Method 1]

After 25 ml of a broth-type medium (Nutrient broth, BD DIFCO., 8 g/L) inoculated with 3,000 CFU/ml bacteria is put into a 50 mL conical tube, 0.015 g of the antibacterial composition is added thereto and suspended (by vortexing), a sufficiently mixed solution is incubated for 16 hours in a shaking water bath maintained at 35° C.

After the incubated solution was diluted to ⅕ using a 1×PBS buffer solution, absorbance (λ=600 nm) was measured using a UV/Vis spectrophotometer, and the antibacterial strength, which is a bacteriostatic reduction rate, is calculated by the following equation by comparing the measured absorbance with a solution incubated without the addition of the antibacterial composition.

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition According to another exemplary embodiment of the present invention, Method 1 is measured against at least one strain of bacteria selected from among *Proteus mirabilis, E. coli, S. aureus, E. cloacae* and *E. faecalis.*

According to still another exemplary embodiment of the present invention, Method 1 is measured for each at least one strain of bacteria for each of *Proteus mirabilis, E. coli, S. aureus, E. cloacae* and *E. faecalis.*

According to yet another exemplary embodiment of the present invention, the antibacterial strength A of the antibacterial composition is expressed within 1 hour, which enables a desired antibacterial strength to be exhibited immediately after application of the antibacterial composition to an intended use or product.

According to yet another exemplary embodiment of the present invention, the ratio (C/B) of the antibacterial strength C measured by the following Method 3 to the antibacterial strength B measured by the following Method 2 of the antibacterial composition is 1 or more and less than 2:

[Method 2]

This method is the same as Method 1, except that 0.005 g of the antibacterial composition is added instead of 0.015 g of the antibacterial composition.

[Method 3]

This method is the same as Method 1, except that 0.02 g of the antibacterial composition is added instead of 0.015 g of the antibacterial composition.

According to yet another exemplary embodiment of the present invention, provided is a product comprising the antibacterial composition, or prepared therefrom.

According to yet another exemplary embodiment of the present invention, provided is a compound selected from among the following Monomers 1 to 10.

Monomer 1

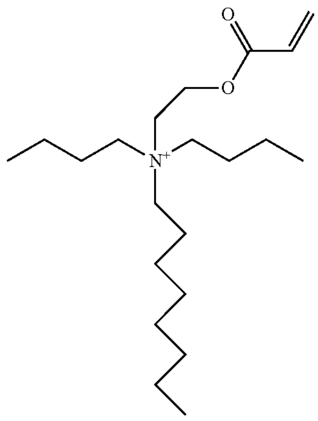

-continued
Monomer 2
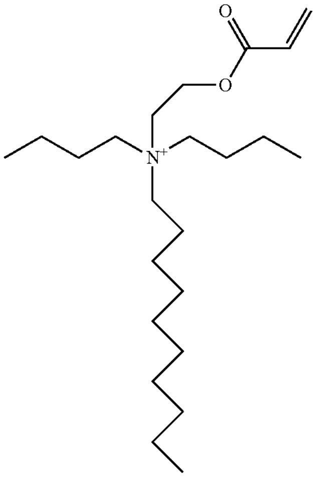
Monomer 3
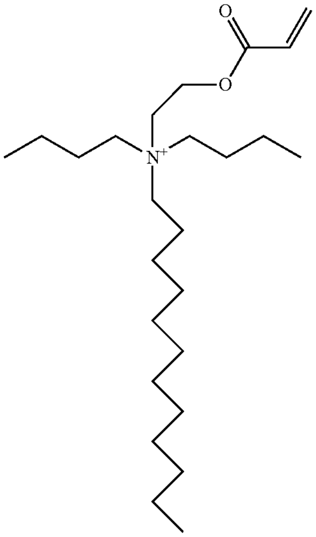
Monomer 4
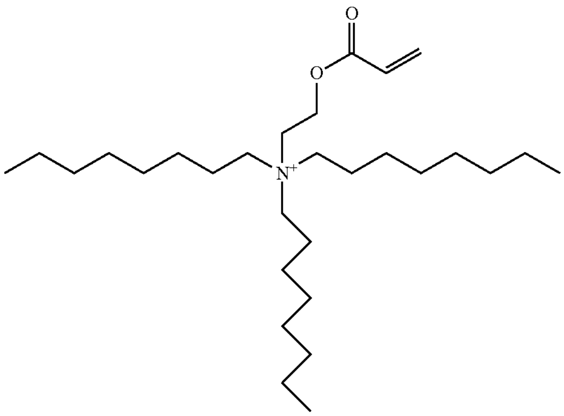
-continued
Monomer 5
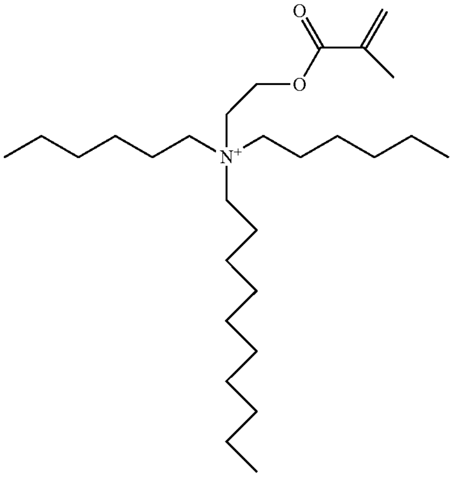
Monomer 6
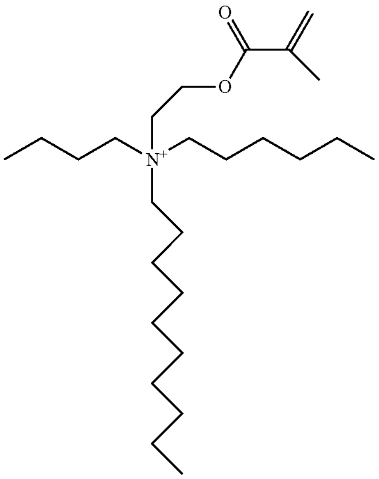
Monomer 7
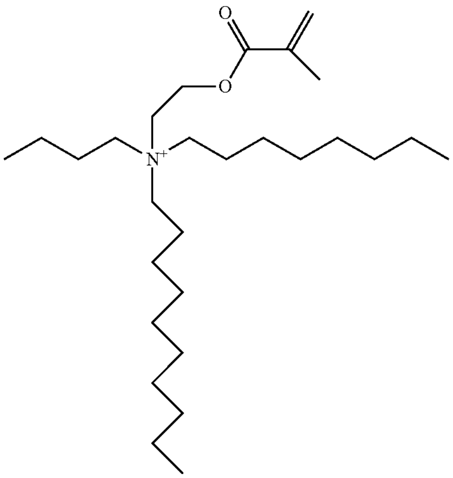

-continued

Monomer 8

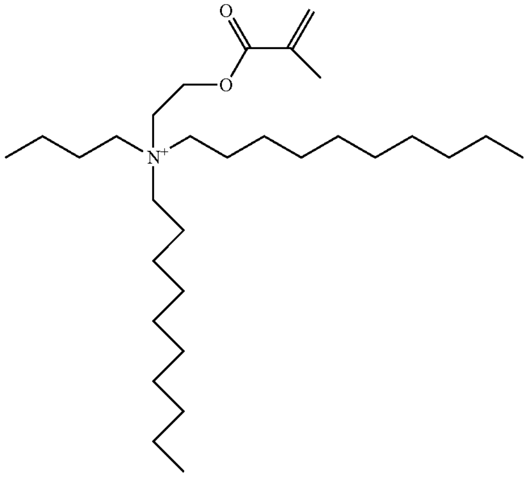

Monomer 9

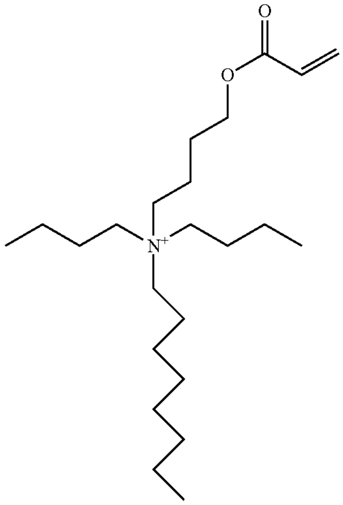

Monomer 10

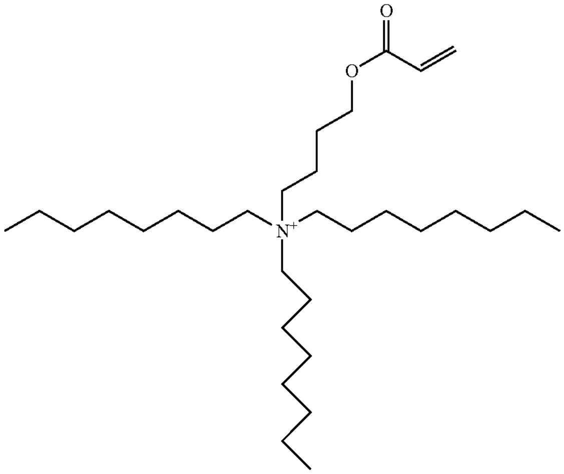

Advantageous Effects

The antibacterial composition according to some exemplary embodiments of the present invention is an antibacterial composition comprising an antibacterial material which has hydrophilicity and hydrophobicity, and thus, is advantageous for imparting antibacterial properties, and is capable of not only imparting antibacterial properties but also solving safety problems due to the leakage of antibacterial materials, by forming a copolymer with an acryl-based resin, has antibacterial properties and acute oral toxicity dose controlled within a characteristic range, and is useful as a material capable of safely imparting excellent antibacterial properties.

The antibacterial composition according to some exemplary embodiments of the present invention can exhibit antibacterial properties within a short period of time.

Since the antibacterial composition according to some exemplary embodiments of the present invention has little change in antibacterial strength depending on the amount of antibacterial material used, antibacterial properties can be exhibited within an expected range even when the unevenness of concentration occurs unintentionally during application to a product.

DETAILED DESCRIPTION

Figure 1:
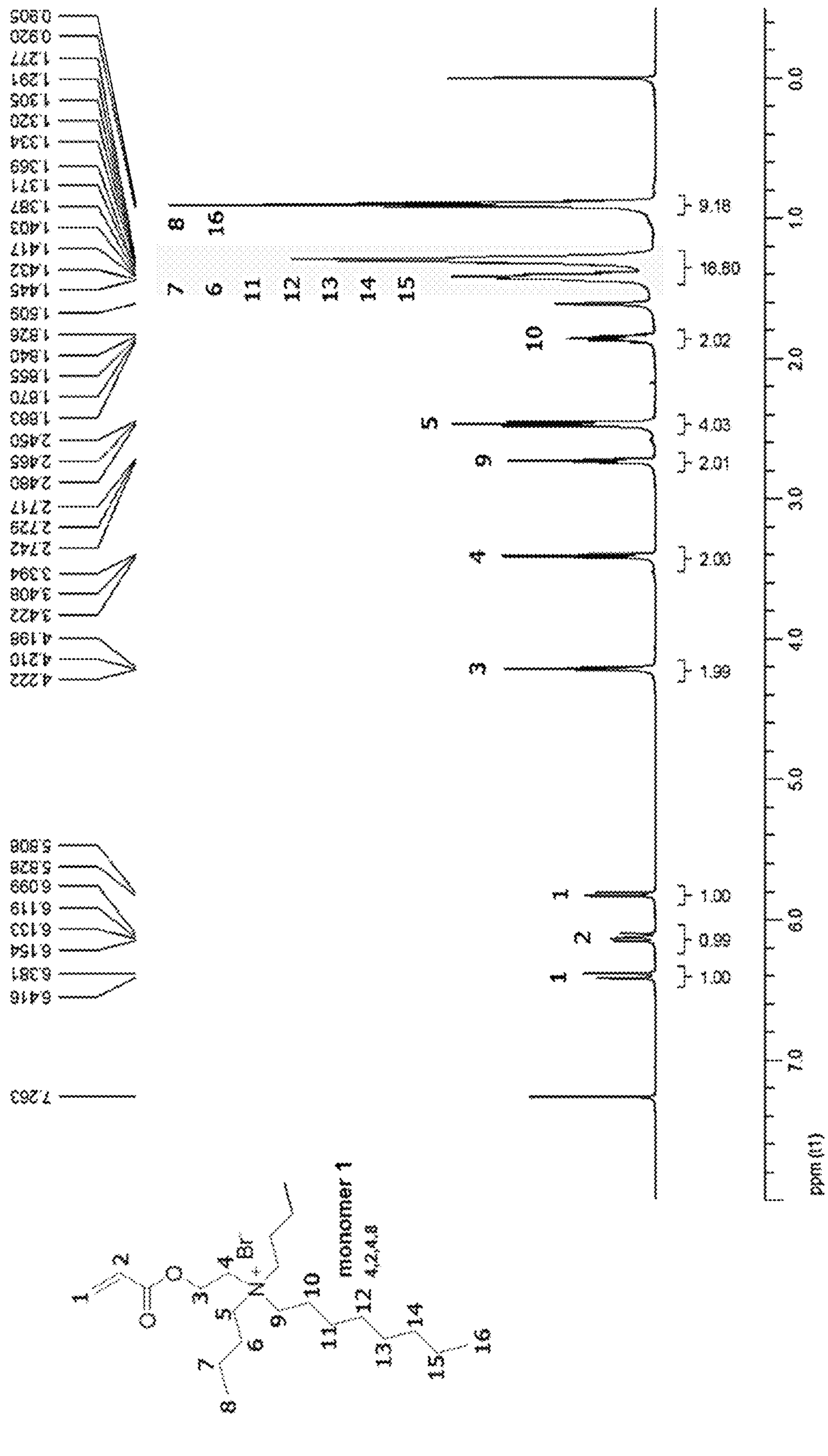
FIG. 1 is a view illustrating the $^1$H-NMR spectrum ($(CD_3)_2SO$) of synthesized Monomer 1 as an exemplary embodiment of the present invention.

An exemplary embodiment of the present invention provides an antibacterial composition comprising at least one compound comprising a quaternary ammonium structure having an acrylate group or a methacrylate group, and having an antibacterial strength A of 90% or more which is measured by the following Method 1 for at least one strain of Gram-positive bacteria and Gram-negative bacteria and an acute oral toxicity dose LD50 of 300 mg/Kg or more:

[Method 1]

After 25 ml of a broth-type medium (Nutrient broth, BD DIFCO., 8 g/L) inoculated with 3,000 CFU/ml bacteria is put into a 50 mL conical tube, 0.015 g of the antibacterial composition is added thereto and suspended (vortexing), a sufficiently mixed solution is incubated for 16 hours in a shaking water bath maintained at 35° C.

After the incubated solution was diluted to ⅕ using a 1×PBS buffer solution, absorbance (λ=600 nm) was measured using a UV/Vis spectrophotometer, and the antibacterial strength, which is a bacteriostatic reduction rate, is calculated by the following equation by comparing the measured absorbance with a solution incubated without the addition of the antibacterial composition.

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition A compound comprising a quaternary ammonium structure having an acrylate group or methacrylate group comprised in the antibacterial composition can physicochemically destruct and kill a cell surface layer structure by hydrophobic interaction, when cations of the ammonium molecule of the quaternary ammonium-based compound are electrostatically adsorbed onto anionic sites of the cell surface of bacteria or microorganisms and a substituent bound to the quaternary ammonium structure is hydrophobic. Further, an antibacterial function can be introduced through copolymerization with an acryl-based resin and the like by the acrylate group or methacrylate group, and in this case, safety can be improved by preventing the antibacterial material from being leaked. According to the exemplary embodiments of the present invention, high antibacterial properties can be safely imparted by comprising compounds having the quaternary ammonium structure as described above and simultaneously limiting the antibacterial strength and acute oral toxicity dose of the antibacterial composition to within a specific range.

The antibacterial strength mentioned in the present specification can be measured for at least one strain of bacteria selected from among *Proteus mirabilis, E. coli, S. aureus, E. cloacae* and *E. faecalis*. Preferably, the antibacterial strength mentioned in the present specification can be measured for at least one strain of bacteria for each of *Proteus mirabilis, E. coli, S. aureus, E. cloacae* and *E. faecalis*. The antibacterial composition according to exemplary embodiments of the present invention can have a certain level or more of antibacterial strength against Gram-positive bacteria and Gram-negative bacteria. ATCC29906 and CCUG4637 can be used as *Proteus mirabilis*, ATCC13047, ATCC13048, and CCUG71839 can be used as *E. Cloaceae*, and ATCC29212 and CCUG9997 can be used as *E. faecalis*.

According to another exemplary embodiment of the present invention, the antibacterial strength A of the antibacterial composition is expressed within 1 hour. This enables a desired antibacterial strength to be exhibited immediately after application of the antibacterial composition to an intended use or product.

According to still another exemplary embodiment of the present invention, the ratio (C/B) of the antibacterial strength C measured by the following Method 3 to the antibacterial strength B measured by the following Method 2 of the antibacterial composition is 1 or more and less than 2.

[Method 2]

This method is the same as Method 1, except that 0.005 g of the antibacterial composition is added instead of 0.015 g of the antibacterial composition.

[Method 3]

This method is the same as Method 1, except that 0.02 g of the antibacterial composition is added instead of 0.015 g of the antibacterial composition.

When an antibacterial composition is applied to the intended use or product, regions of unintentionally high concentration and low concentration of the antibacterial material can occur, and a region of low concentration may not exhibit the desired antibacterial properties. However, according to the exemplary embodiments, since there is little change in antibacterial strength depending on the amount of antibacterial material used, antibacterial properties can be exhibited within an expected range even when the unevenness of concentration occurs unintentionally during application to an intended use or product.

According to yet another exemplary embodiment of the present invention, the antibacterial strength A is 99% or more, preferably 99.3% or more, more preferably 99.5% or more, even more preferably 99.7% or more, and still even more preferably 99.9% or more.

According to yet another exemplary embodiment of the present invention, an antibacterial strength D measured by the following Method 4 is 65% or more.

[Method 4]

This method is the same as Method 1, except that 0.01 g of the antibacterial composition is added instead of 0.015 g of the antibacterial composition.

According to the exemplary embodiments, excellent antibacterial properties can be provided even when the antibacterial composition is added in an amount of 0.01 g.

According to another exemplary embodiment of the present invention, the antibacterial strength D can be 65% or more, 68% or more, 68.2% or more, and 70% or more. Further, the antibacterial strength D can be 99% or more, preferably 99.3% or more, more preferably 99.5% or more, even more preferably 99.7% or more, and still even more preferably 99.9% or more.

According to still another exemplary embodiment of the present invention, an antibacterial strength B measured by the following Method 2 is 55% or more.

[Method 2]

This method is the same as Method 1, except that 0.005 g of the antibacterial composition is added instead of 0.015 g of the antibacterial composition.

According to the exemplary embodiments, excellent antibacterial properties can be provided even when the antibacterial composition is added in an amount of 0.005 g.

According to another exemplary embodiment of the present invention, the antibacterial strength B can be 55% or more, 59% or more, 59.3% or more, 60% or more, and 61.2% or more. In addition, the antibacterial strength B can be 99% or more, preferably 99.3% or more, more preferably 99.5% or more, even more preferably 99.7% or more, and still even more preferably 99.9% or more.

According to still another exemplary embodiment of the present invention, the antibacterial composition according to the above-described exemplary embodiments has an acute oral toxicity dose LD50 of 300 mg/Kg or more, more than 300 mg/Kg, 500 mg/Kg or more, preferably 800 mg/Kg or more, and more preferably 1,000 mg/Kg or more. According to specific examples, the antibacterial composition according to the above-described exemplary embodiments can have an acute oral toxicity dose LD50 of 800 mg/Kg or more, 843 mg/Kg or more, 869 mg/Kg or more, 900 mg/Kg or more, or 998 mg/Kg or more. The antibacterial composition according to the above-described exemplary embodiments can have an acute oral toxicity dose LD50 of 1,000 mg/Kg or more, 1,050 mg/Kg or more, 1,078 mg/Kg or more, 1,100 mg/Kg or more, 1,111 mg/Kg or more, 1,200 mg/Kg or more, 1,242 mg/Kg or more, 1,300 mg/Kg or more, 1,369 mg/Kg or more, 1,400 mg/Kg or more, 1,442 mg/Kg or more, 1,498 mg/Kg or more, 1,500 mg/Kg or more, 1,600 mg/Kg or more, 1,700 mg/Kg or more, and 1,708 mg/Kg or more. According to specific examples, the antibacterial composition according to the above-described exemplary embodiments can have an acute oral toxicity dose LD50 of 843 mg/Kg, 869 mg/Kg, 998 mg/Kg, 1,078 mg/Kg, 1,111 mg/Kg, 1,242 mg/Kg, 1,369 mg/Kg, 1,442 mg/Kg, 1,498 mg/Kg, or 1,708 mg/Kg.

The higher the acute oral toxicity dose LD50 of the antibacterial composition according to the above-described exemplary embodiments, the lower the toxicity, so that the acute oral toxicity dose is advantageous. However, the value of LD50 can be determined from the viewpoint that the above-described antibacterial strength needs also be satisfied. For example, the antibacterial composition according to the above-described exemplary embodiments can have an acute oral toxicity dose LD50 of 50,000 mg/Kg or less, for example, 10,000 mg/Kg or less, 5,000 mg/Kg or less, or 2,000 mg/Kg or less. According to an example, the antibacterial composition according to the above-described exemplary embodiments can have an acute oral toxicity dose LD50 of 1,708 mg/Kg or less.

According to another exemplary embodiment of the present invention, the antibacterial composition according to the above-described exemplary embodiments has an acute percutaneous toxicity dose LD50 of 1,000 mg/Kg or more, more than 1,000 mg/Kg, preferably 1,500 mg/Kg or more, and more preferably 2,000 mg/Kg or more. The higher the acute percutaneous toxicity dose LD50 of the antibacterial composition according to the above-described exemplary embodiments, the lower the toxicity, so that the acute percutaneous toxicity dose is advantageous.

According to an exemplary embodiment of the present invention, the compound comprising a quaternary ammonium structure having an acrylate group or methacrylate group can be selected from among those capable of exhibiting the above-described antibacterial strength and acute oral toxicity dose LD50 from among the compounds of Chemical Formula 1:

[Chemical Formula 1]

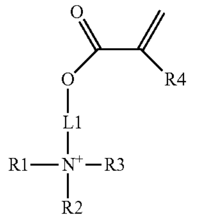

wherein in Chemical Formula 1:

L1 is an alkylene group having 2 to 4 carbon atoms;

R1, R2 and R3 are the same as or different from each other, and are each an alkyl group having 1 to 20 carbon atoms; and R4 is hydrogen or a methyl group.

According to an exemplary embodiment, at least of R1, R2 and R3 of Chemical Formula 1 is an alkyl group having 8 or more carbon atoms, preferably an alkyl group having 8 to 14 carbon atoms, and more preferably an alkyl group having 8 to 12 carbon atoms.

According to an exemplary embodiment, the sum of the number of carbon atoms of the alkyl group comprised in R1, R2 and R3 of Chemical Formula 1 is 12 to 24.

According to an exemplary embodiment, the sum of the number of carbon atoms of two of R1, R2 and R3 having the higher number of carbon atoms in Chemical Formula 1 is 2 to 24, preferably 8 to 20, and more preferably 8 to 16. According to an example, the sum of the number of carbon atoms of two of R1, R2 and R3 having the higher number of carbon atoms in Chemical Formula 1 can be 9 to 15.

According to an exemplary embodiment, the number of carbon atoms of the alkyl group having the largest number of carbon atoms in R1, R2 and R3 of Chemical Formula 1 is 12 or less, preferably 11 or less.

According to an exemplary embodiment, when any one of two having the largest number of carbon atoms among R1, R2 and R3 of Chemical Formula 1 has 10 or more carbon atoms, the other has less than 8 carbon atoms.

Here, when a group having the largest number of carbon atoms is selected, any one is selected in the case where there are groups having the same number of carbon atoms.

Acute oral toxicity and acute percutaneous toxicity can be controlled when having the number of carbon atoms according to the aforementioned exemplary embodiments. When acute oral toxicity and/or acute percutaneous toxicity are too high, there are restrictions on intended uses, particularly use in infant products such as diapers.

According to an exemplary embodiment, L1 in Chemical Formula 1 is ethylene or butylene.

According to an exemplary embodiment, R4 in Chemical Formula 1 is hydrogen.

According to an exemplary embodiment, R4 in Chemical Formula 1 is methyl.

The antibacterial composition can be composed of only a compound comprising the quaternary ammonium structure having an acrylate group or methacrylate group, and an additive or solvent can be additionally added, if necessary.

According to another exemplary embodiment of the present invention, the compound comprising the quaternary ammonium structure having the acrylate group or methacrylate group has a water solubility of 50% or more, preferably 60% or more. The solubility can be measured at room temperature.

According to still another exemplary embodiment of the present invention, the compound comprising the quaternary ammonium structure having an acrylate group or methacrylate group has an ethanol solubility of 50% or more, preferably 60% or more. The solubility can be measured at room temperature.

According to yet another exemplary embodiment of the present invention, the compound comprising the quaternary ammonium structure having an acrylate group or methacrylate group can be dissolved in at least one of methanol, acetone, dichloromethane, DMSO, THF, and chloroform, and preferably can be dissolved in each of them.

According to yet another exemplary embodiment of the present invention, the compound comprising the quaternary ammonium structure having an acrylate group or methacrylate group can be selected from among the following Monomers 1 to 10:

Monomer 1

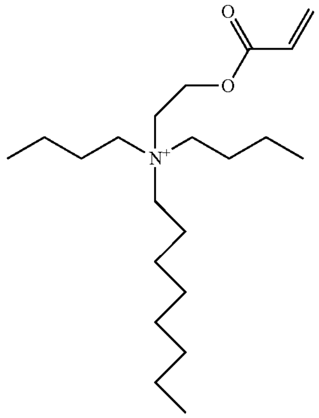

-continued
Monomer 2
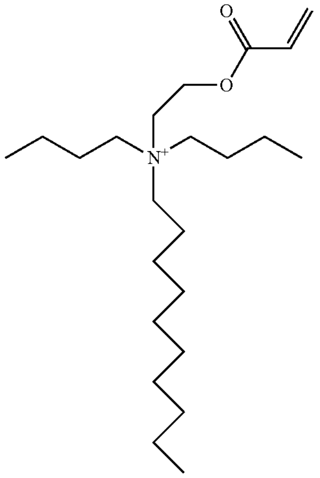
Monomer 3
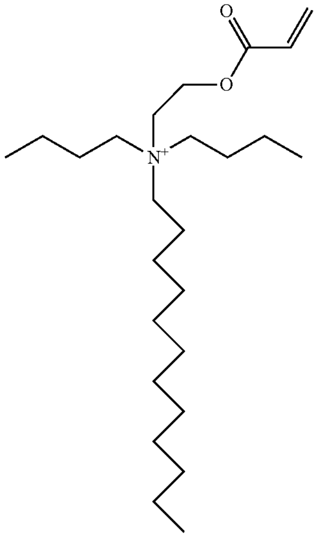
Monomer 4
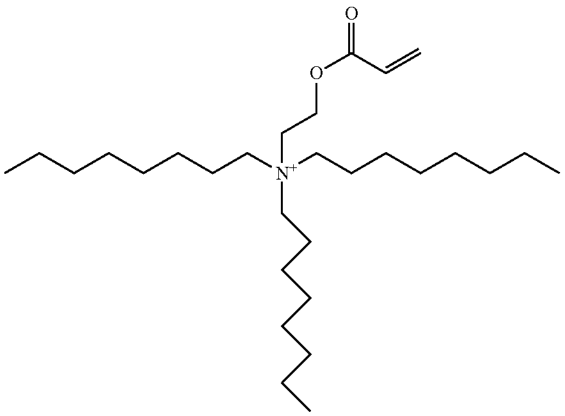
-continued
Monomer 5
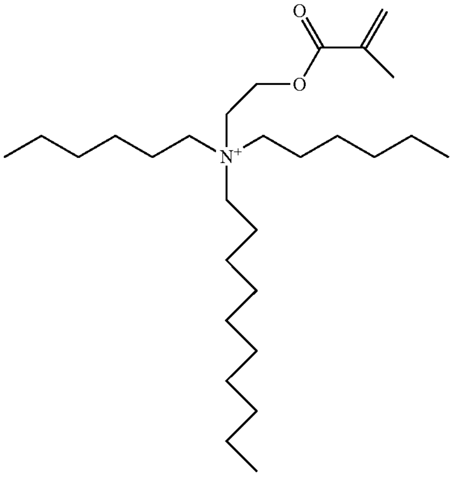
Monomer 6
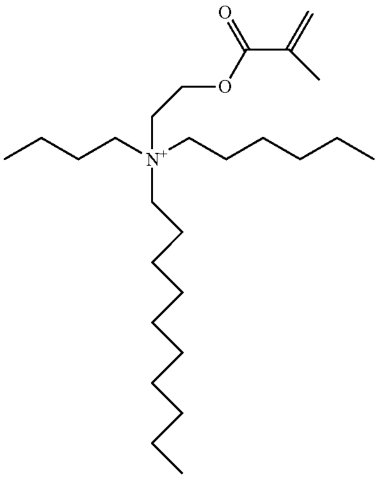
Monomer 7
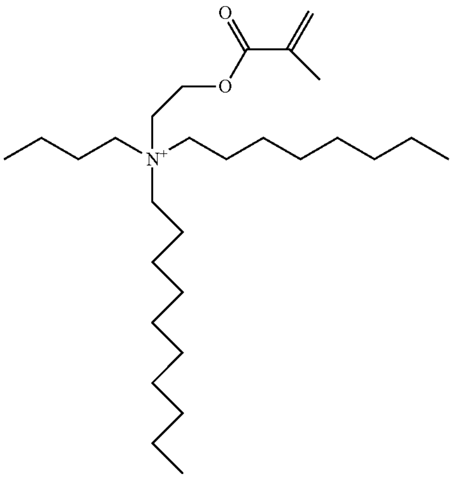

-continued

Monomer 8

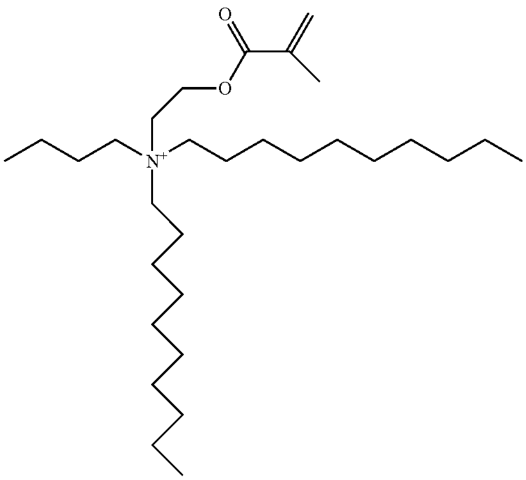

Monomer 9

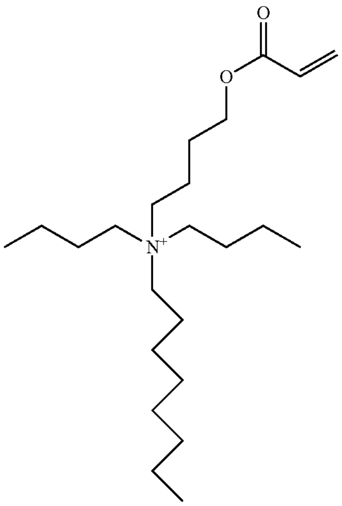

Monomer 10

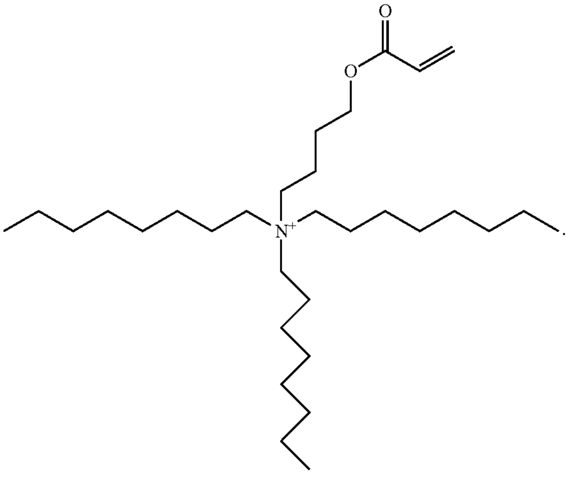

The antibacterial composition according to the above-described exemplary embodiments or the compound comprising the quaternary ammonium structure having an acrylate group or methacrylate group comprised in the same can be present in the form of a powder or oil.

Since the compound comprising the quaternary ammonium structure having an acrylate group or methacrylate group exhibits cationic properties, the compound can be present in a form where a salt is formed along with a group exhibiting anionic properties. In this case, the group exhibiting anionic properties is not particularly limited, and materials known in the art can be used as long as the materials do not impair the purpose of the antibacterial composition. For example, the group exhibiting anionic properties can be a halogen anion, specifically, $Br^-$.

According to yet another exemplary embodiment of the present invention, provided is a product comprising the antibacterial composition according to the above-described exemplary embodiments or prepared therefrom. The product is not particularly limited as long as antibacterial properties are required. According to an example, the product can be used in a state of a copolymer such as a copolymer with a (meth)acrylate-based resin, a copolymer with polyvinyl chloride, a copolymer with polylactic acid (PLA), and a copolymer with urethane, or can be a product comprising at least one of the copolymers, for example, a hygiene product, an antibacterial film, a diaper, and the like. The copolymer is preferably a copolymer with an acrylate or methacrylate-based compound. As the copolymerization method, a known copolymerization method can be applied.

According to yet another exemplary embodiment of the present invention, provided is a compound selected from among the following Monomers 1 to 10. The same description on the above-described compound comprising the quaternary ammonium structure having an acrylate group or methacrylate group can be applied to the following Monomers 1 to 10.

Monomer 1

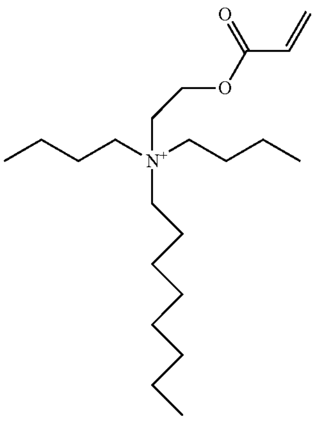

-continued
Monomer 2
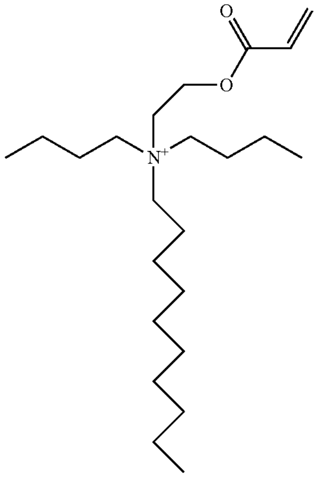
Monomer 3
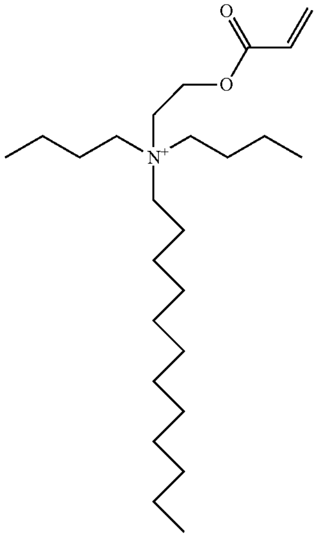
Monomer 4
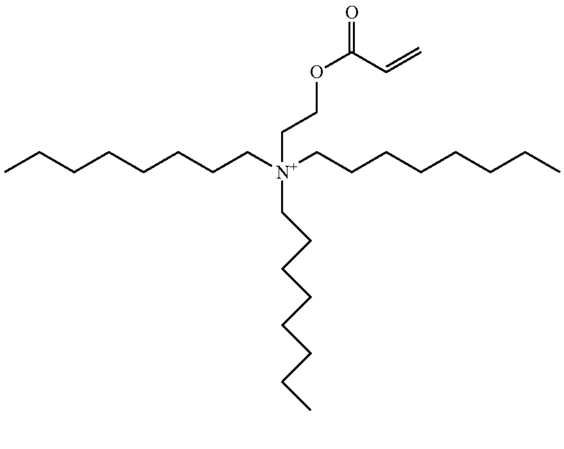
-continued
Monomer 5
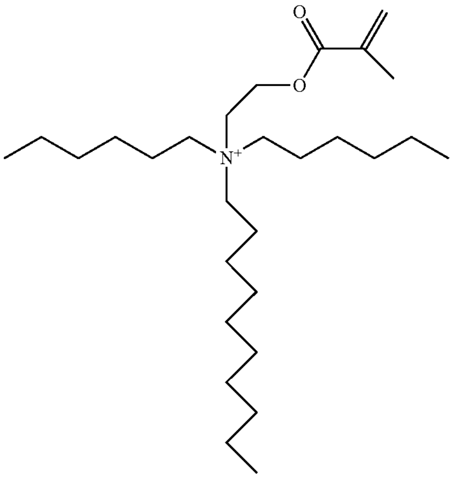
Monomer 6
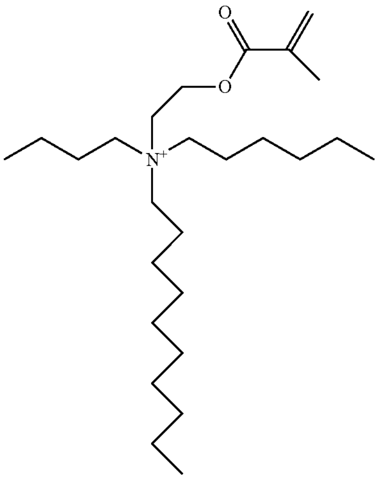
Monomer 7
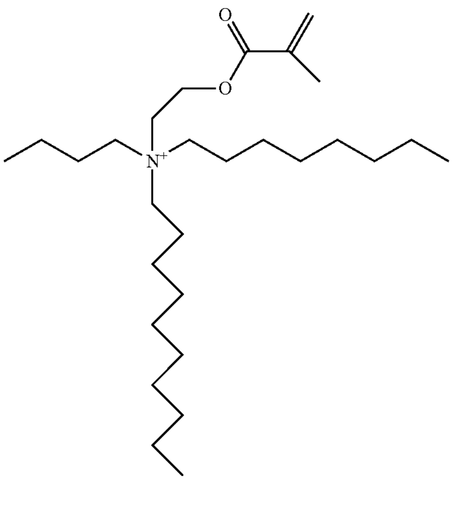

-continued

Monomer 8

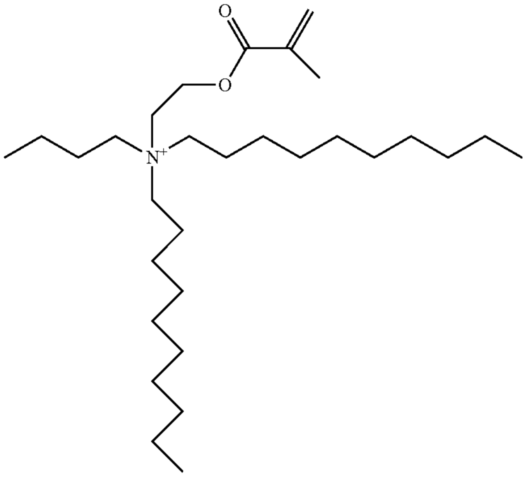

Monomer 9

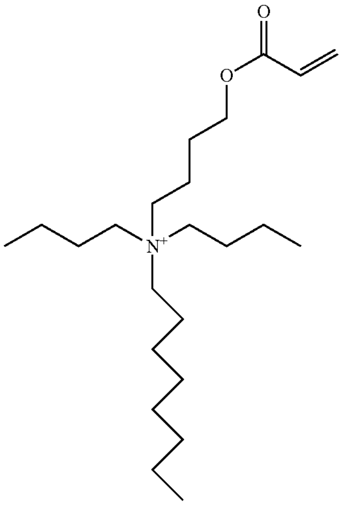

Monomer 10

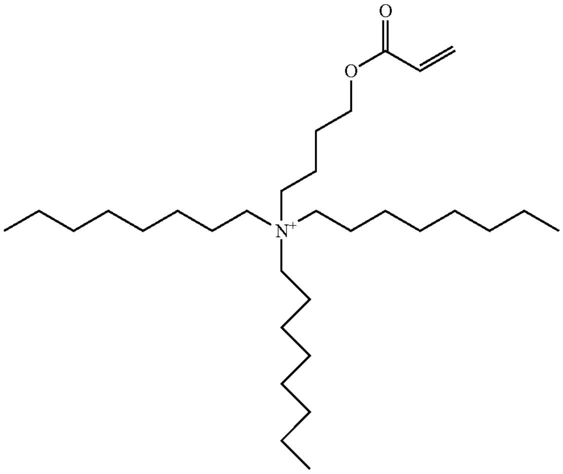

A compound selected from among Monomers 1 to 10 can be applied as a constituent component of the antibacterial composition. Furthermore, since the compound selected among Monomers 1 to 10 exhibits cationic properties, the compound can be present in a form where a salt is formed along with a group exhibiting anionic properties. In this case, the group exhibiting anionic properties is not particularly limited, and materials known in the art can be used as long as the materials do not impair the purpose of the antibacterial composition. For example, the group exhibiting anionic properties can be a halogen anion, specifically, $Br^-$.

EXAMPLES

Hereinafter, the present invention will be described in more detail through examples. However, the following examples are provided for illustrating the present invention, and the scope of the present invention is not limited thereby.

Synthesis of Compound Comprising Quaternary Ammonium Structure

Synthesis of Monomer 1, Monomer 2, and Monomer 3

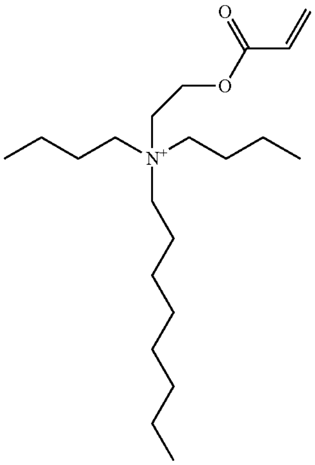

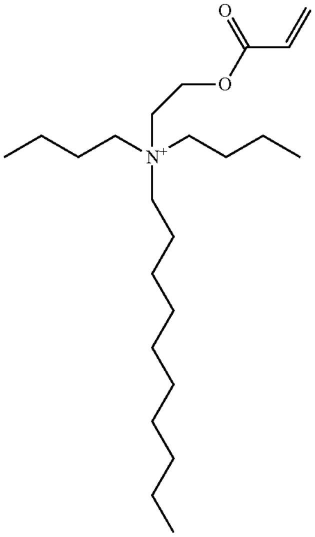

-continued

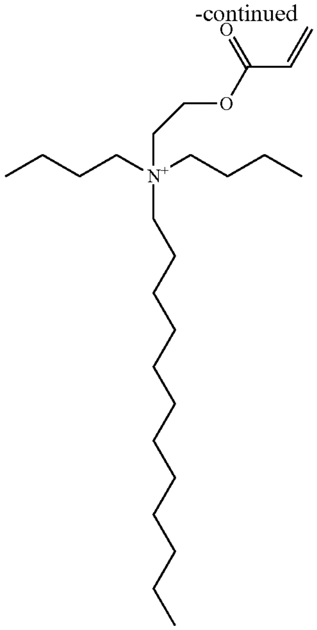

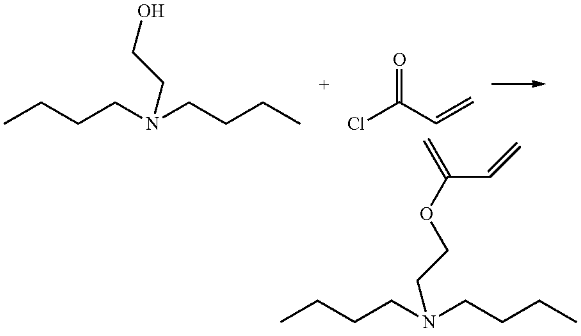

Step 1

1. 0.1 mol of 2-(dibutylamino)ethanol (DBAE), 0.1 mol of trimethylamine and 0.001 mol of hydroquinone were added to 100 mL of THF (solvent).
2. 0.1 mol of acryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromooctane (preparation of Monomer 1), 1-bromodecane (preparation of Monomer 2), or 1-bromododecane (preparation of Monomer 3) were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered. Here, although a static precipitation method of adding a reactant to a nonsolvent was used, a reverse precipitation method of adding a nonsolvent to a reactant can also be used. Furthermore, in addition to 15:1, other ratios of MTBE and reaction solution can be used, and for example, 12:1 and 26:1 can be used.
5. The resulting product was dried under vacuum at 45° C.

Figure 2:
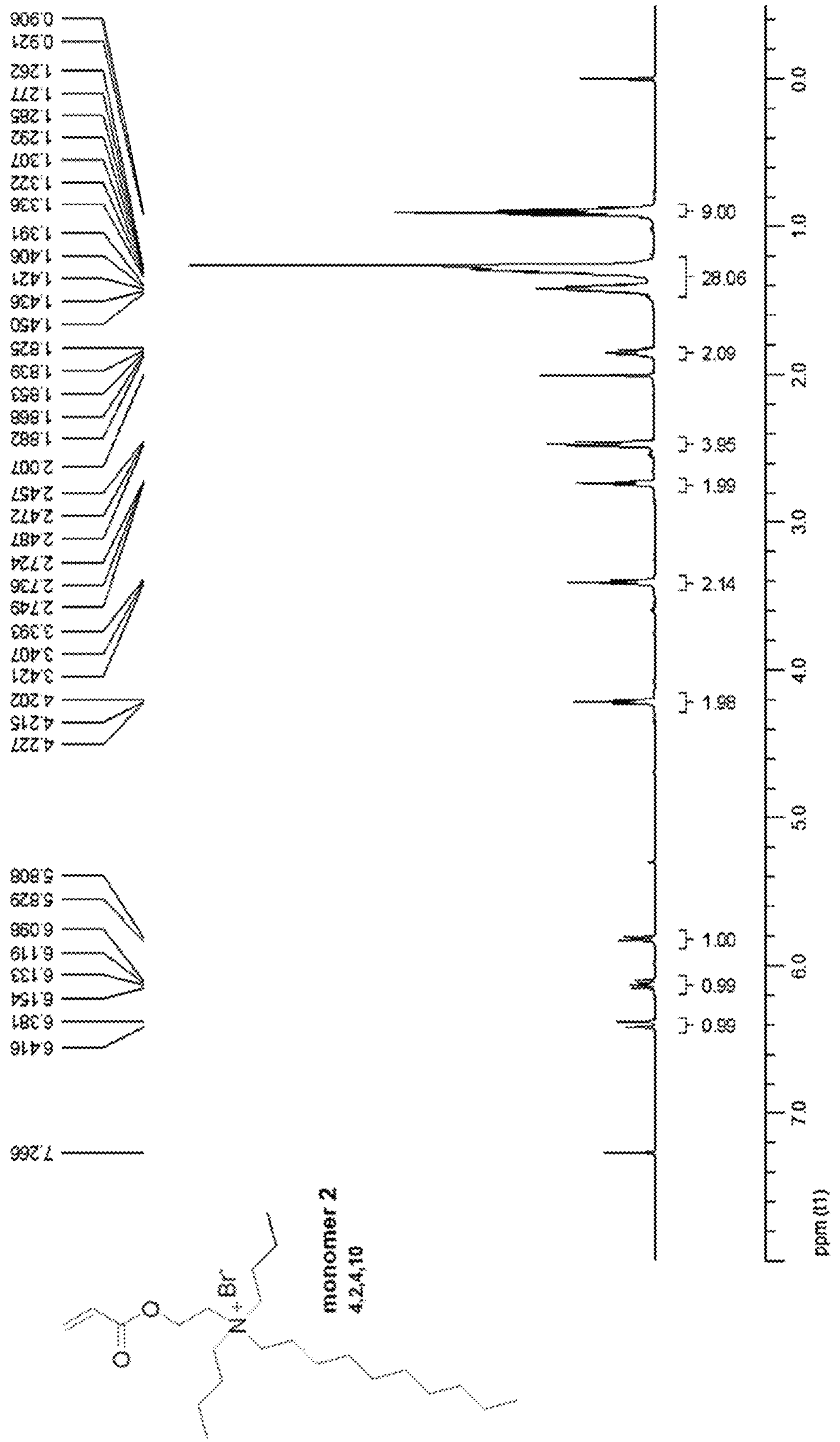
FIG. 2 is a view illustrating the $^1$H-NMR spectrum ($(CD_3)_2SO$) of synthesized Monomer 2 as an exemplary embodiment of the present invention.
Figure 3:
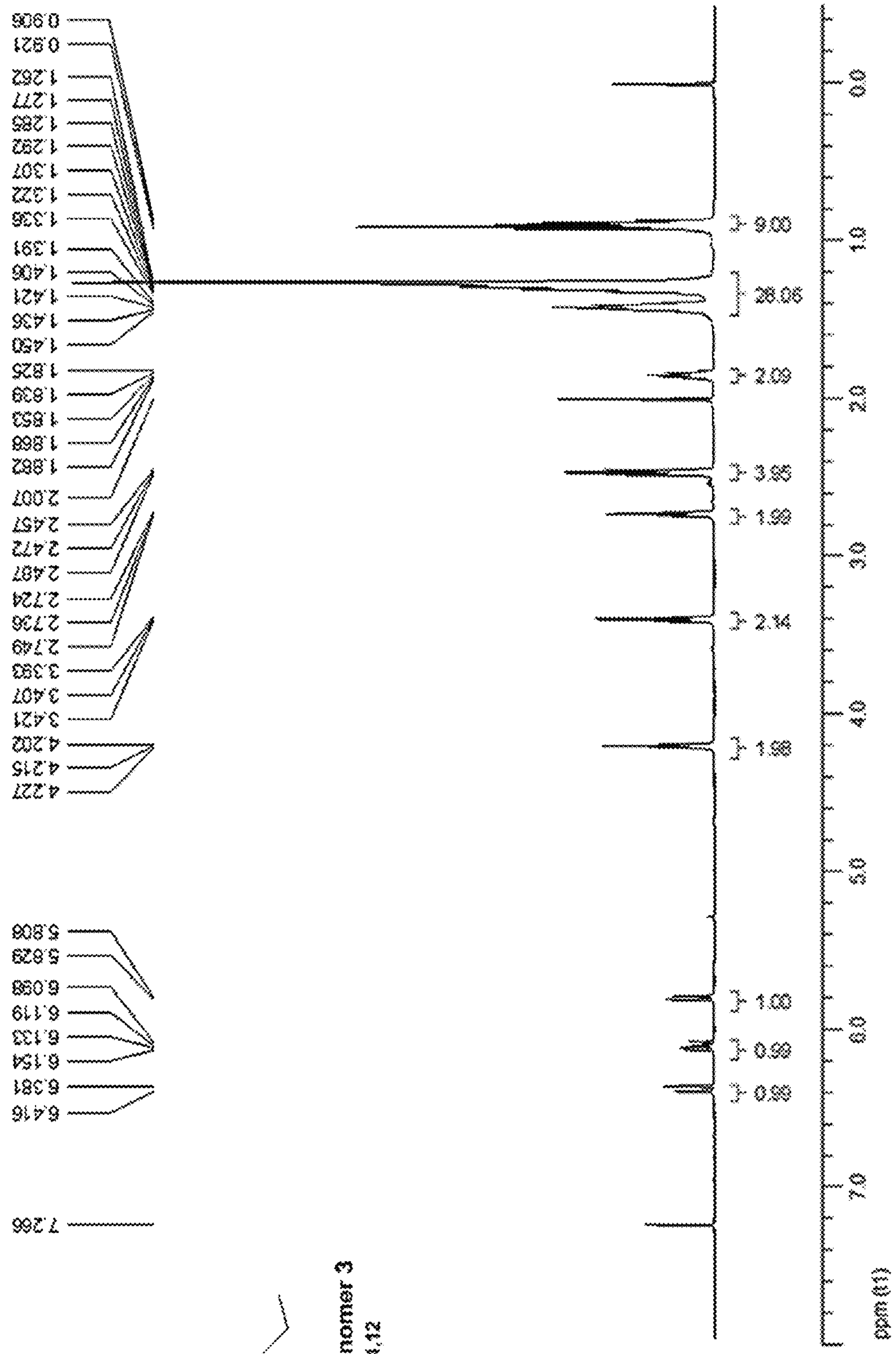
FIG. 3 is a view illustrating the $^1$H-NMR spectrum ($(CD_3)_2SO$) of synthesized Monomer 3 as an exemplary embodiment of the present invention.
Figure 3:
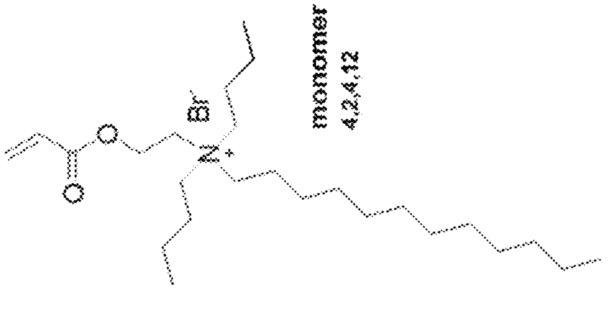

The $^{1}H$-NMR spectrum ($(CD_3)_2SO$) of the synthesized Monomer 1 is illustrated in the following FIG. 1, the $^{1}H$-NMR spectrum ($(CD_3)_2SO$) of the synthesized Monomer 2 is illustrated in the following FIG. 2, and the $^{1}H$-NMR spectrum ($(CD_3)_2SO$) of the synthesized Monomer 3 is illustrated in FIG. 3.

Synthesis of Monomer 4

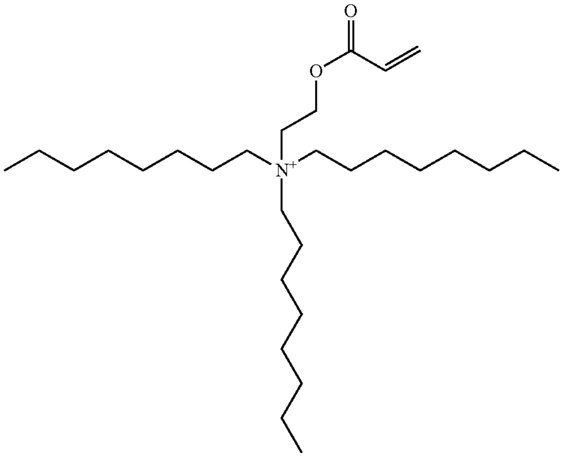

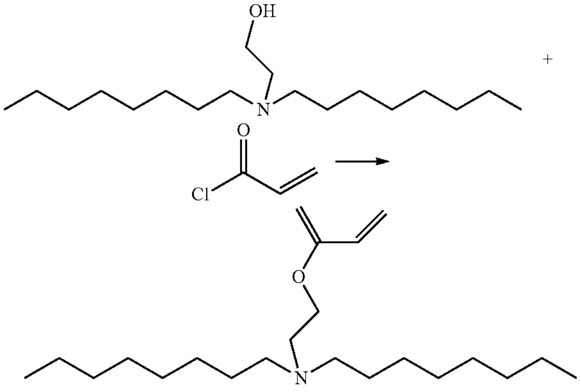

Step 1

1. 0.1 mol of 2-(dioctylamino)ethanol (DOAE), 0.1 mol of trimethylamine and 0.001 mol of hydroquinone were added to 100 mL of THF (solvent).
2. 0.1 mol of acryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromooctane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.

4. After static precipitation (MTBE:reaction solution=15:1) in methyl t-butyl ether (MTBE), the mixture was filtered.
5. The resulting product was dried under vacuum at 45° C.

Synthesis of Monomer 4 was confirmed by $^1$H-NMR spectrum $(CD_3)_2SO)$ in a manner similar to the above-described Monomers 1 to 3.

Synthesis of Monomer 5

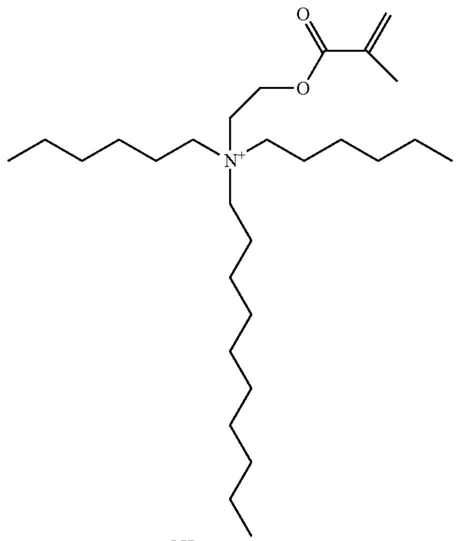

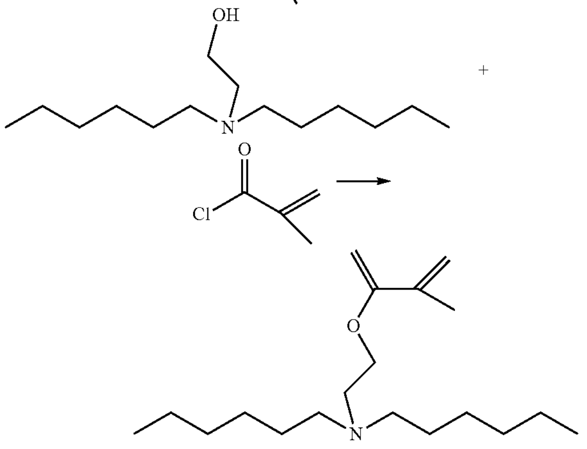

Step 1

1. 0.1 mol of 2-(dihexylamino)ethanol (DHAE), 0.1 mol of trimethylamine and 0.001 mol of hydroquinone were added to 100 mL of THF (solvent).
2. 0.1 mol of methacryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromodecane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of monomer 5 was confirmed by $^1$H-NMR spectrum $(CD_3)_2SO)$ in a manner similar to the above-described Monomers 1 to 3.

Synthesis of Monomer 6

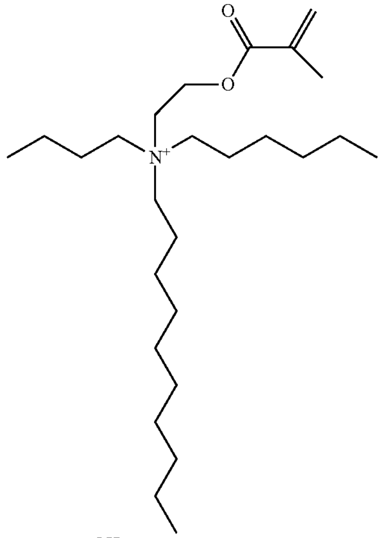

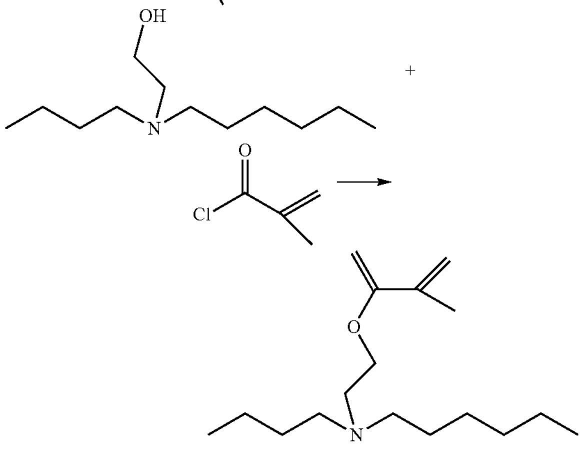

Step 1

1. 0.1 mol of (butylhexylamino)ethanol (BHAE), 0.1 mol of trimethylamine and 0.001 mol of hydroquinone were added to 100 mL of THF (solvent).
2. 0.1 mol of methacryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromodecane were dissolved at 50 wt % in acrylonitrile (solvent) at a ratio of 1:1.

2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of Monomer 6 was confirmed by $^1$H-NMR spectrum ($(CD_3)_2SO$) in a manner similar to the above-described Monomer 1 to 3.

Synthesis of Monomer 7

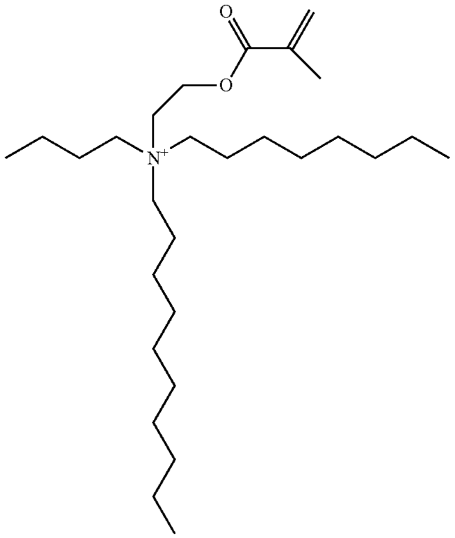

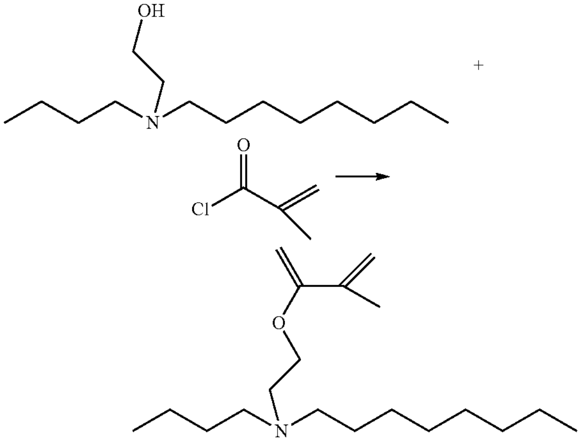

Step 1

1. 0.1 mol of 2-(butyloctylamino)ethanol (BOAE), 0.1 mol of trimethylamine and 0.001 mol of hydroquinone were added to 100 mL of THF (solvent).
2. 0.1 mol of methacryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromodecane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of Monomer 7 was confirmed by $^1$H-NMR spectrum ($(CD_3)_2SO$) in a manner similar to the above-described Monomer 1 to 3.

Synthesis of Monomer 8

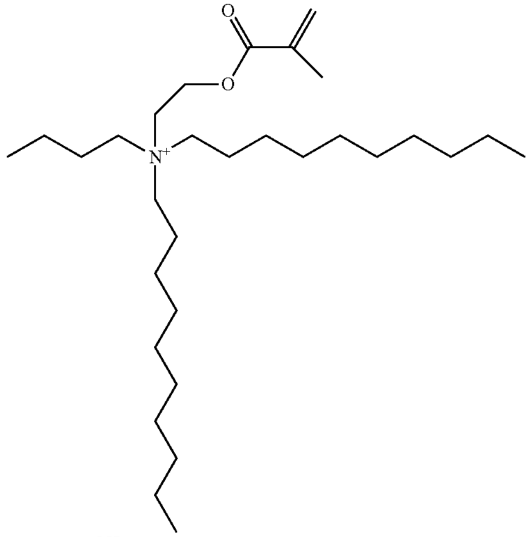

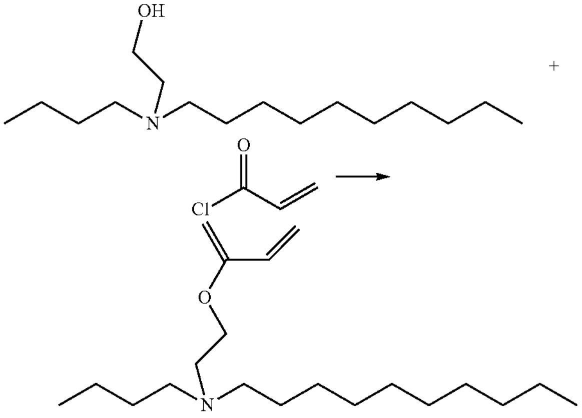

Step 1

1. 0.1 mol of 2-(butyldecylamino)ethanol (BOAE), 0.1 mol of trimethylamine and 0.001 mol of hydroquinone were added to 100 mL of THF (solvent).
2. 0.1 mol of methacryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.

5. The residue was dried under vacuum at 83 to 87° C.

Step 2

1. The product of Step 1 and 1-bromodecane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of Monomer 8 was confirmed by $^{1}$H-NMR spectrum ($(CD_3)_2SO$) in a manner similar to the above-described Monomer 1 to 3.

Synthesis of Monomer 9

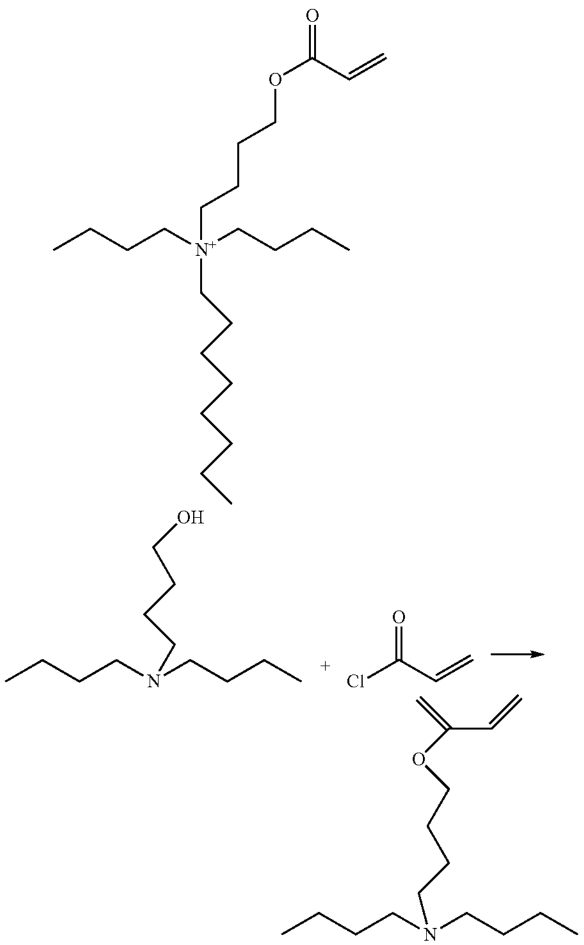

Step 1

1. 0.1 mol of 2-(dibutylamino)butanol (DBAB), 0.1 mol of trimethylamine and 0.001 mol of hydroquinone were added to 100 mL of THF (solvent).
2. 0.1 mol of acryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromooctane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of Monomer 9 was confirmed by $^{1}$H-NMR spectrum ($(CD_3)_2SO$) in a manner similar to the above-described Monomers 1 to 3.

Synthesis of Monomer 10

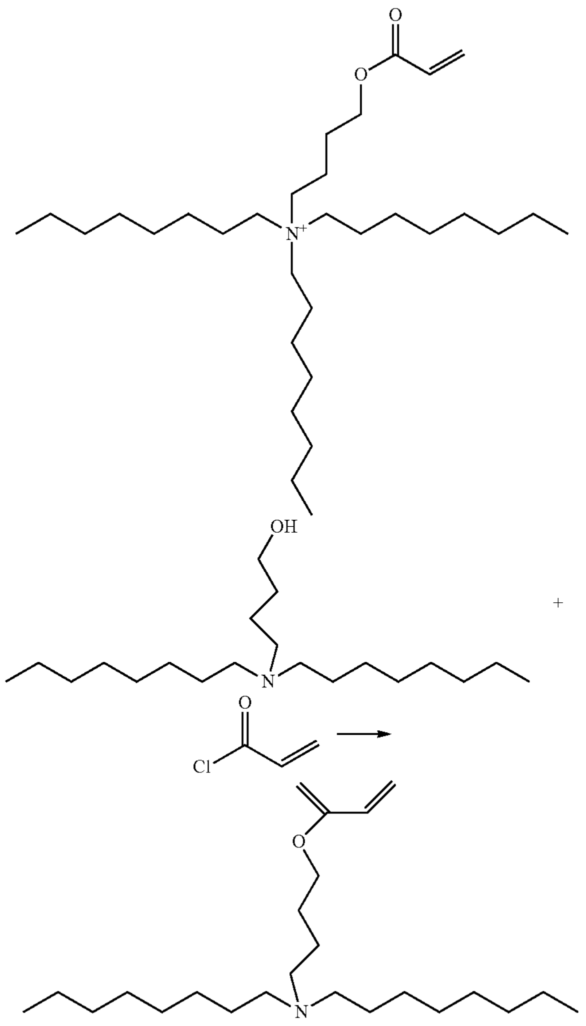

Step 1

1. 0.1 mol 2-(dioctylamino)butanol (DOAB), 0.1 mol of trimethylamine and 0.001 mol of hydroquinone were added to 100 mL of THF (solvent).

2. 0.1 mol of acryloyl chloride was added dropwise onto a reaction solution while stirring the materials (room temperature).
3. The resulting mixture was stirred for 2 hours.
4. After a triethylamine salt was removed by filtering the mixture, the solvent was removed by a rotary evaporator.
5. The residue was dried under vacuum at 83 to 87° C.

Step 2

1. The product of Step 1 and 1-bromooctane were dissolved at 50 wt % in acrylonitrile (solvent) at a ratio of 1:1.
2. Subsequently, p-methoxyphenol, which is a polymerization inhibitor, was added (ratio with reactants 1:0.001 eq).
3. The resulting mixture was reacted at 50° C. for 20 hours.
4. After static precipitation (MTBE:reaction solution=15:1) in methyl t-butyl ether (MTBE), the mixture was filtered.
5. The resulting product was dried under vacuum at 45° C.

Synthesis of Monomer 10 was confirmed by $^1$H-NMR spectrum ($(CD_3)_2SO$) in a manner similar to the above-described Monomer 1 to 3.

Synthesis of Comparative Monomer 1

Synthesis was performed in the same manner as in the synthesis process of Monomer 1, except that bromohexane was used instead of 1-bromooctane of Step 2 in the synthesis process of Monomer 1.

Synthesis of Comparative Monomer 1 was confirmed by $^1$H-NMR spectrum ($(CD_3)_2SO$) in a manner similar to the above-described Monomers 1 to 3.

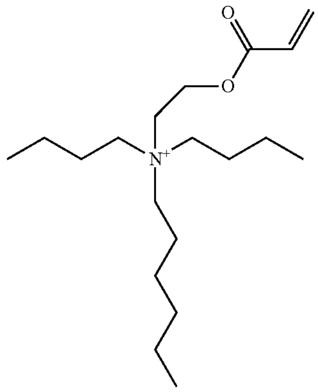 [SMILES: C=CC(=O)OCC[N+](CCCC)(CCCC)CCCCCC]

Synthesis of Comparative Monomer 2

Synthesis was performed in the same manner as in the synthesis process of Monomer 10, except that 2-(ditetradecylamino)butanol was used instead of 2-(dioctylamino) butanol of Step 1 and bromotetradecane was used instead of 1-bromooctane of Step 2 in the synthesis process of Monomer 10.

Synthesis of Comparative Monomer 2 was confirmed by $^1$H-NMR spectrum ($(CD_3)_2SO$) in a manner similar to the above-described Monomers 1 to 3.

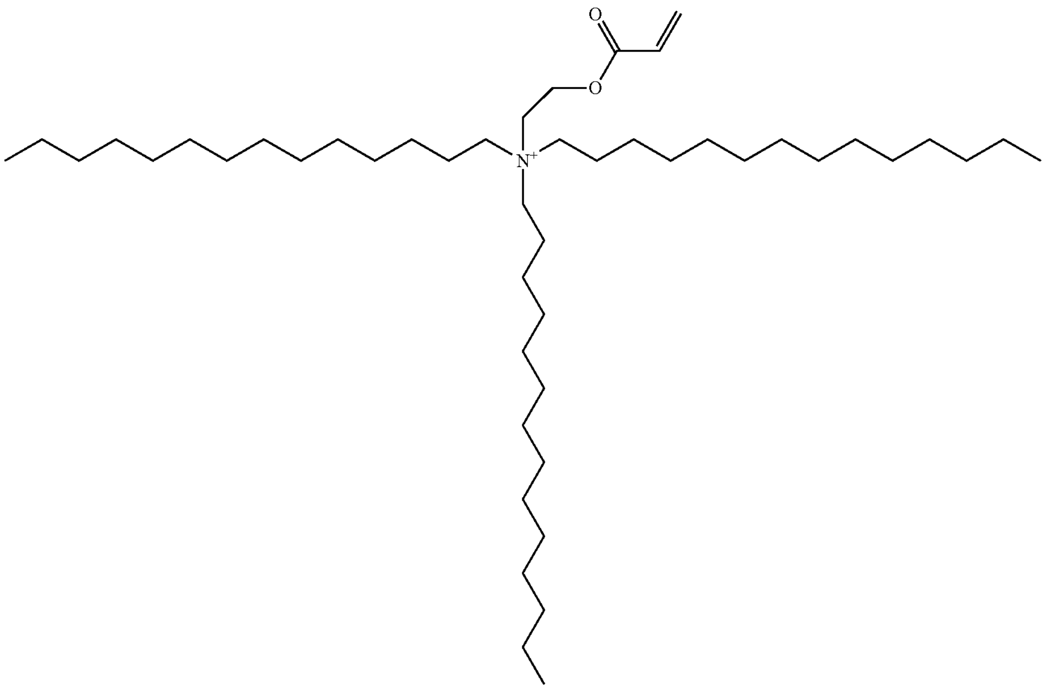 [SMILES: C=CC(=O)OCC[N+](CCCCCCCCCCCCCC)(CCCCCCCCCCCCCC)CCCCCCCCCCCCCC]

The antibacterial strength of Monomers 1 to 10 and Comparative Monomers 1 and 2 by Methods 1 to 4 was measured, and is shown in the following Table 1. In this case, the *P. mirabilis* (ATCC29906) bacteria were used.

TABLE 1

| | | Antibacterial strength (%) | | | |
|---|---|---|---|---|---|
| No. | Sample | Method 2 (amount of antibacterial composition added 0.005 g) | Method 4 (amount of antibacterial composition added 0.01 g) | Method1 (amount of antibacterial composition added 0.015 g) | Method 3 (amount of antibacterial composition added 0.02 g) |
| 1 | reference | — | — | — | — |
| 2 | Monomer 1 | 59.3 | 68.2 | 99.9 | 99.9 |
| 3 | Monomer 2 | 99.9 | 99.9 | 99.9 | 99.9 |
| 4 | Monomer 3 | 99.9 | 99.9 | 99.9 | 99..9 |
| 5 | Monomer 4 | 99.9 | 99.9 | 99.9 | 99.9 |
| 6 | Monomer 5 | 99.9 | 99.9 | 99.9 | 99.9 |
| 7 | Monomer 6 | 99.9 | 99.9 | 99.9 | 99.9 |
| 8 | Monomer 7 | 99.9 | 99.9 | 99.9 | 99.9 |
| 9 | Monomer 8 | 99.9 | 99.9 | 99.9 | 99.9 |
| 10 | Monomer 9 | 61.2 | 70.0 | 99.9 | 99.9 |
| 11 | Monomer 10 | 99.9 | 99.9 | 99.9 | 99.9 |
| 12 | Comparative Monomer 1 | 22.6 | 30.7 | 38.8 | 46.9 |
| 13 | Comparative Monomer 2 | 99.9 | 99.9 | 99.9 | 99.9 |

According to Table 1, all Monomers 1 to 10 had an antibacterial strength A of 99.9% measured by Method 1.

The time at which 99.9% of the antibacterial strength of Monomers 1 to 10 and Comparative Monomers 1 and 2 is confirmed is shown in the following Table 2.

TABLE 2

| | | Antibacterial strength (%) | | | |
|---|---|---|---|---|---|
| No. | Sample | Method 2 (amount of antibacterial composition added 0.005 g) | Method 4 (amount of antibacterial composition added 0.01 g) | Method 1 (amount of antibacterial composition added 0.015 g) | Method 3 (amount of antibacterial composition added 0.02 g) |
| 1 | reference | — | — | — | — |
| 2 | Monomer 1 | — | — | Within 1 hour | Within 1 hour |
| 3 | Monomer 2 | Within 1 hour | Within 1 hour | Within 1 hour | Within 1 hour |
| 4 | Monomer 3 | Within 1 hour | Within 1 hour | Within 1 hour | Within 1 hour |
| 5 | Monomer 4 | Within 1 hour | Within 1 hour | Within 1 hour | Within 1 hour |
| 6 | Monomer 5 | Within 1 hour | Within 1 hour | Within 1 hour | Within 1 hour |
| 7 | Monomer 6 | Within 1 hour | Within 1 hour | Within 1 hour | Within 1 hour |
| 8 | Monomer 7 | Within 1 hour | Within 1 hour | Within 1 hour | Within 1 hour |
| 9 | Monomer 8 | Within 1 hour | Within 1 hour | Within 1 hour | Within 1 hour |
| 10 | Monomer 9 | — | — | Within 1 hour | Within 1 hour |
| 11 | Monomer 10 | Within 1 hour | Within 1 hour | Within 1 hour | Within 1 hour |
| 12 | Comparative Monomer 1 | — | — | — | — |
| 13 | Comparative Monomer 2 | Within 1 hour | Within 1 hour | Within 1 hour | Within 1 hour |

According to Table 2, all Monomers 1 to 10 having an antibacterial strength A of 99.9% measured by Method 1 was confirmed within 1 hour.

The acute oral toxicity dose LD50 of Monomers 1 to 10 and Comparative Monomers 1 and 2 is shown in the following Table 3.

TABLE 3

| Sample | Acute oral toxicity dose (mg/Kg) LD50 |
|---|---|
| Monomer 1 | 1,708 |
| Monomer 2 | 1,369 |

TABLE 3-continued

| Sample | Acute oral toxicity dose (mg/Kg) LD50 |
|---|---|
| Monomer 3 | 843 |
| Monomer 4 | 1,442 |
| Monomer 5 | 1,078 |
| Monomer 6 | 1,111 |
| Monomer 7 | 998 |
| Monomer 8 | 869 |
| Monomer 9 | 1,498 |
| Monomer 10 | 1,242 |
| Comparative Monomer 1 | 2,355 |
| Comparative Monomer 2 | 231 |

According to Table 3, all Monomers 1 to 10 had an acute oral toxicity dose LD50 of 300 mg/Kg or more, particularly 800 mg/Kg or more. Furthermore, Examples 1, 2, 4, 5, 6, 9 and 10 had an acute oral toxicity dose LD50 of 1,000 mg/Kg or more.

The acute percutaneous toxicity dose LD50 of Monomers 1 to 10 is shown in the following Table 4.

TABLE 4

| Sample | Acute percutaneous toxicity dose (mg/Kg) LD50 |
|---|---|
| Monomer 1 | 2,000 or more |
| Monomer 2 | 2,000 or more |
| Monomer 3 | 2,000 or more |
| Monomer 4 | 2,000 or more |
| Monomer 5 | 2,000 or more |
| Monomer 6 | 2,000 or more |
| Monomer 7 | 2,000 or more |
| Monomer 8 | 2,000 or more |
| Monomer 9 | 2,000 or more |
| Monomer 10 | 2,000 or more |

According to Table 4, all Monomers 1 to 10 had an acute percutaneous toxicity dose LD50 of 1,000 mg/Kg or more, particularly 2,000 mg/Kg or more.

Figure 4:
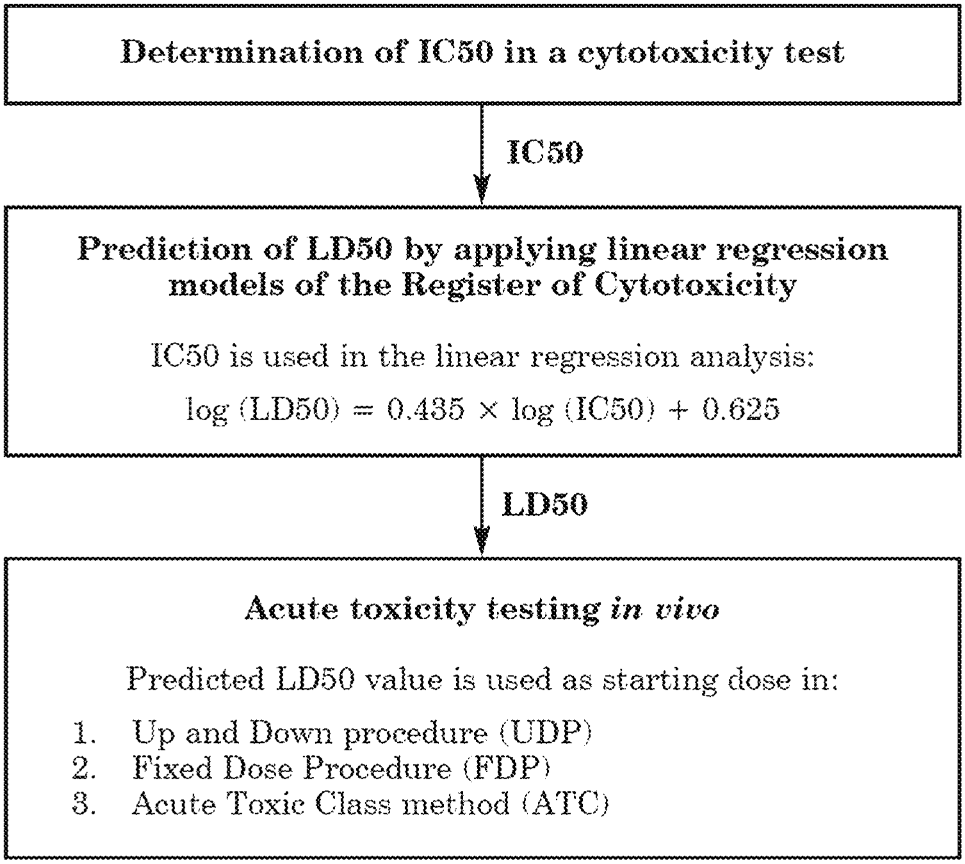
FIG. 4 is a flowchart showing a method for calculating acute oral toxicity dose LD50 and acute percutaneous toxicity dose LD50.

The acute oral toxicity dose LD50 and acute percutaneous toxicity dose LD50 were measured by 3T3 Neutral Red Uptake (NRU) assay (OECD Guidance Document No 129). Specifically, the acute oral toxicity dose LD50 and acute percutaneous toxicity dose LD50 can be calculated by the method shown in FIG. 4.

The invention claimed is:

1. An antibacterial composition comprising at least one compound of the following Chemical Formula 1 comprising a quaternary ammonium structure having an acrylate group or methacrylate group, and having an antibacterial strength A of 90% or more which is measured by the following Method 1 for at least one strain of Gram-positive bacteria and at least one strain of Gram-negative bacteria, and having an acute oral toxicity dose LD50 of 300 mg/Kg or more:

[Chemical Formula 1]

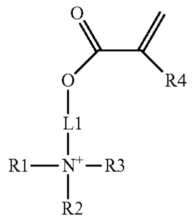

wherein in Chemical Formula 1:

L1 is an alkylene group having 2 to 4 carbon atoms;

R1, R2 and R3 are the same as or different from each other, and are each an alkyl group having 4 to 20 carbon atoms; and R4 is hydrogen or a methyl group, wherein the Chemical Formula 1 is associated with an anion that does not impair the antibacterial strength of the composition;

[Method 1]

putting 25 ml of a nutrient broth medium inoculated with 3,000 CFU/ml bacteria into a 50 ml conical tube, and adding 0.015 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 ml conical tube and vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength λ of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition.

2. The antibacterial composition of claim 1, wherein Method 1 is measured against at least one strain of bacteria selected from among *Proteus mirabilis, E. coli, S. aureus, E. cloacae* and *E. faecalis.*

3. The antibacterial composition of claim 1, wherein Method 1 is measured for at least one strain of bacteria for each of *Proteus mirabilis, E. coli, S. aureus, E. cloacae* and *E. faecalis.*

4. The antibacterial composition of claim 1, wherein the antibacterial strength A of the antibacterial composition is exhibited immediately after application of the antibacterial composition.

5. The antibacterial composition of claim 1, wherein a ratio (C/B) of an antibacterial strength C measured by the following Method 3 to an antibacterial strength B measured by the following Method 2 is 1 or more to less than 2:

[Method 2]

putting 25 ml of a nutrient broth medium inoculated with 3,000 CFU/ml bacteria into a 50 ml conical tube, and adding 0.005 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 mL conical tube vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength 2 of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition

[Method 3]

putting 25 ml of a nutrient broth medium inoculated with 3,000 CFU/ml bacteria into a 50 ml conical tube, and adding 0.02 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 mL conical tube vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength 2 of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition.

6. The antibacterial composition of claim 1, wherein the antibacterial strength A is 99% or more.

7. The antibacterial composition claim 1, wherein an antibacterial strength D measured by the following Method 4 is 65% or more:

[Method 4]

putting 25 ml of a nutrient broth medium inoculated with 3,000 CFU/ml bacteria into a 50 mL conical tube, and adding 0.01 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 mL conical tube vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength 2 of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition.

8. The antibacterial composition of claim 7, wherein the antibacterial strength D is 99% or more.

9. The antibacterial composition of claim 1, wherein an antibacterial strength B measured by the following Method 2 is 55% or more:

[Method 2]

putting 25 ml of a nutrient broth medium inoculated with 3,000 CFU/ml bacteria into a 50 ml conical tube, and adding 0.005 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 mL conical tube vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength 2 of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition.

10. The antibacterial composition of claim 9, wherein the antibacterial strength B is 99% or more.

11. The antibacterial composition of claim 1, wherein the acute oral toxicity dose LD50 is 800 mg/Kg or more.

12. The antibacterial composition of claim 1, wherein the acute oral toxicity dose LD50 is 1,000 mg/Kg or more.

13. The antibacterial composition of claim 1, wherein at least one of R1, R2 and R3 of Chemical Formula 1 is an alkyl group having 8 or more carbon atoms, and the sum of the number of carbon atoms of the alkyl groups included in R1, R2 and R3 is 16 to 24.

14. The antibacterial composition of claim 1, wherein the compound comprising the quaternary ammonium structure having an acrylate group or methacrylate group is selected among the following Monomers 1 to 10:

-continued
Monomer 1
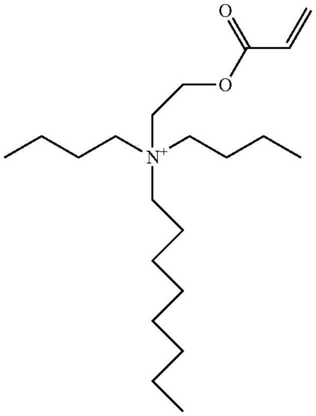
Monomer 2
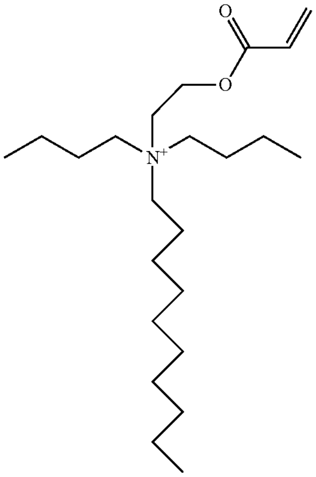
Monomer 3
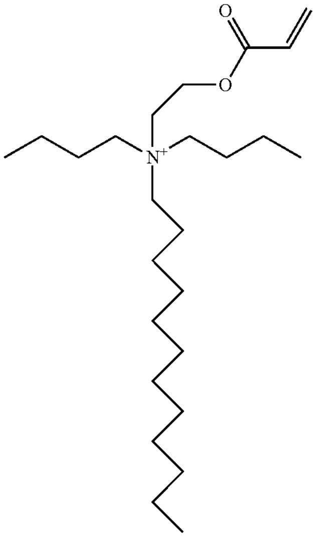
Monomer 4
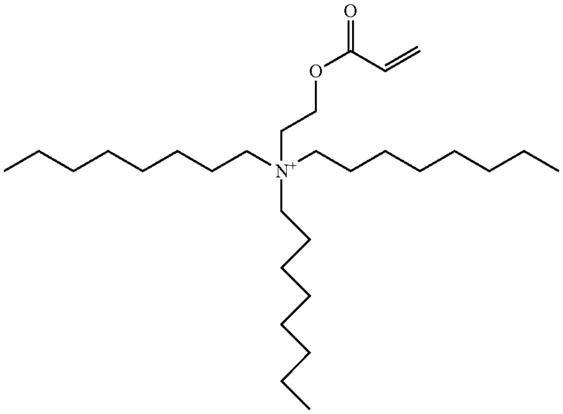
Monomer 5
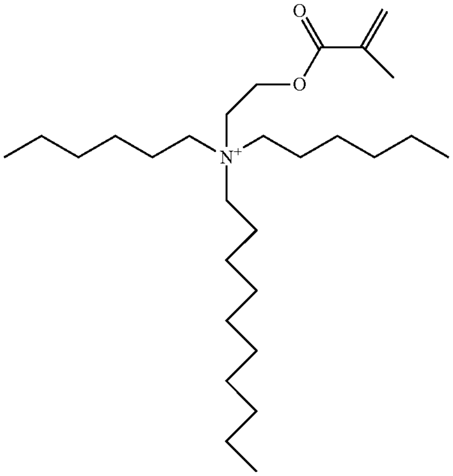
Monomer 6
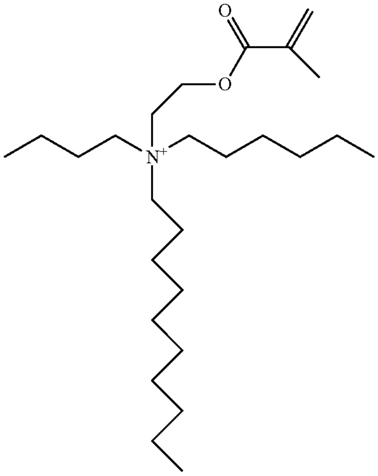

-continued

Monomer 7

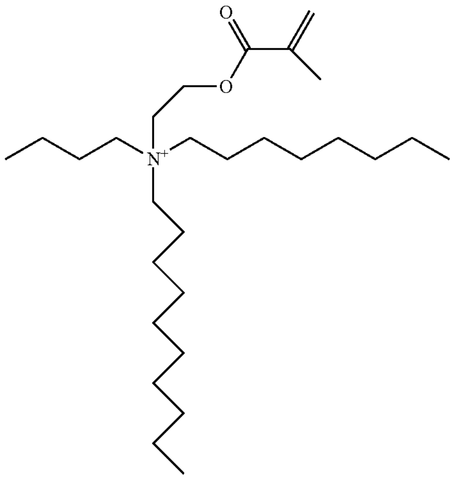

Monomer 8

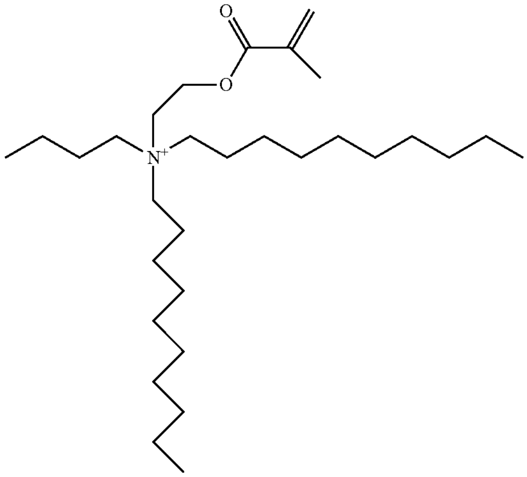

Monomer 9

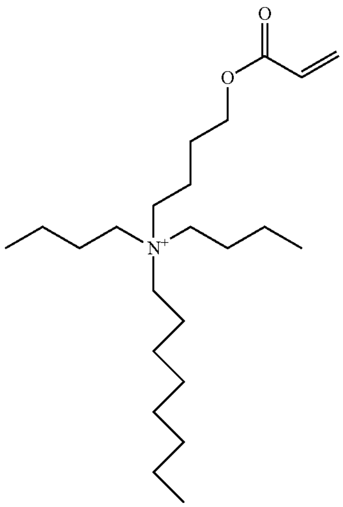

-continued

Monomer 10

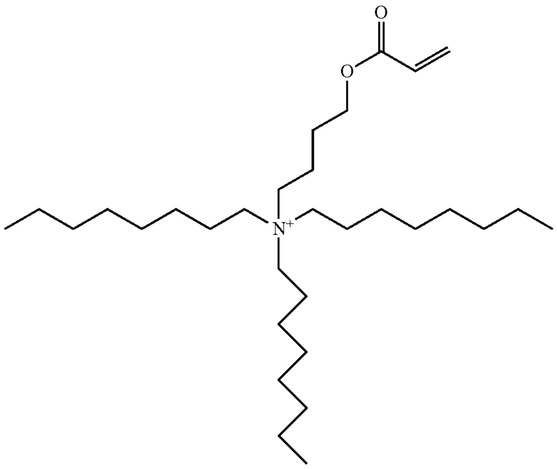

wherein each of the Monomers 1 to 10 is associated with an anion that does not impair the antibacterial strength of the composition.

15. An antibacterial composition comprising at least one compound of the following Chemical Formula 1 comprising a quaternary ammonium structure having an acrylate group or methacrylate group, and having an antibacterial strength A of 90% or more which is measured by the following Method 1 for at least one strain of Gram-positive bacteria and at least one strain of Gram-negative bacteria, and having an acute percutaneous toxicity dose LD50 of 1,000 mg/Kg or more;

[Chemical Formula 1]

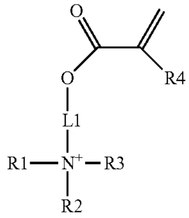

wherein in Chemical Formula 1:

L1 is an alkylene group having 2 to 4 carbon atoms;

R1, R2 and R3 are the same as or different from each other, and are each an alkyl group having 4 to 20 carbon atoms; and R4 is hydrogen or a methyl group, wherein the Chemical Formula 1 is associated with an anion that does not impair the antibacterial strength of the composition;

[Method 1]

putting 25 ml of a nutrient broth medium inoculated with 3,000 CFU/ml bacteria into a 50 ml conical tube, and adding 0.015 g of the antibacterial composition thereto and vortexing to yield a mixed solution that is incubated for 16 hours in a shaking water bath maintained at 35° C. to form an incubated solution;

putting 25 ml of a nutrient broth medium inoculated with 3,000 CFU/ml bacteria into a 50 mL conical tube and vortexing to yield a mixed solution that is incubated for 16 hours in a shaking water bath maintained at 35° C. to form a reference solution;

diluting each of the incubated solution and the reference solution to ⅕ using a 1× PBS buffer solution; and measuring absorbance measured at a wavelength 2 of 600 nm using a UV/Vis spectrophotometer, and the antibacterial strength, which is a bacteriostatic reduction rate, is calculated by the following equation by comparing the measured absorbance of the incubated solution with the reference solution which is a solution incubated without the addition of the antibacterial composition:

$$\text{Antibacterial strength}(\%)=(1-A_{sample}/A_{Reference})\times 100$$

$A_{sample}$=Absorbance of medium solution incubated by adding antibacterial composition $A_{Reference}$=Absorbance of medium solution incubated without addition of antibacterial composition.

16. The antibacterial composition of claim 15, wherein the antibacterial composition has an acute percutaneous toxicity dose LD50 of 2,000 mg/Kg or more.

17. A product, comprising the antibacterial composition of claim 1, or prepared therefrom.

18. A compound selected from among the following Monomers 1 to 10:

Monomer 1

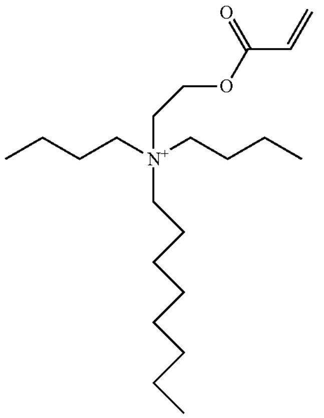

Monomer 2

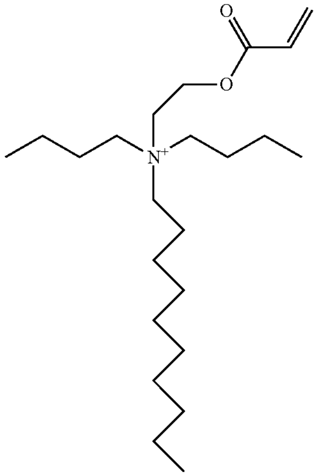

-continued

Monomer 3

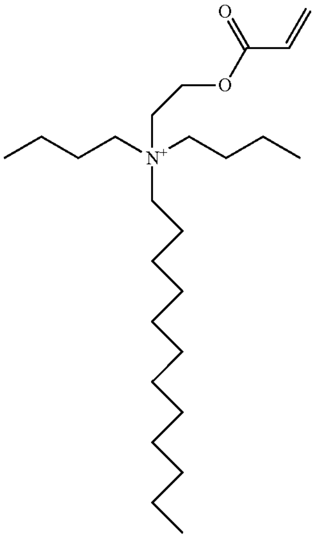

Monomer 4

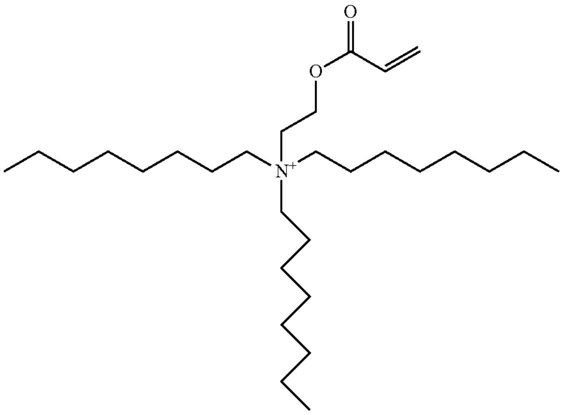

Monomer 5

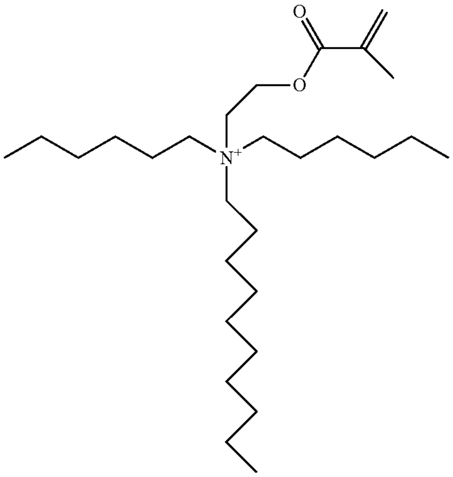

-continued
Monomer 6
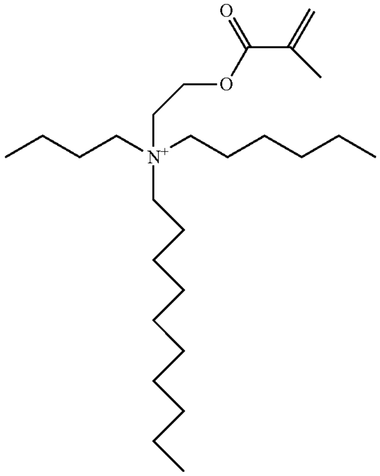
Monomer 7
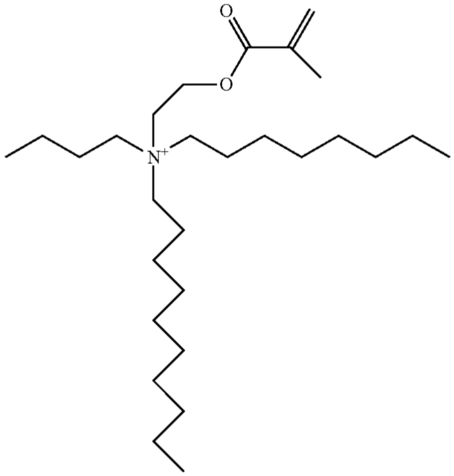
Monomer 8
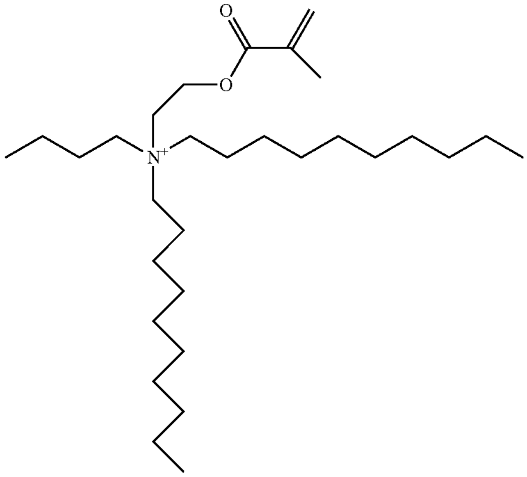
-continued
Monomer 9
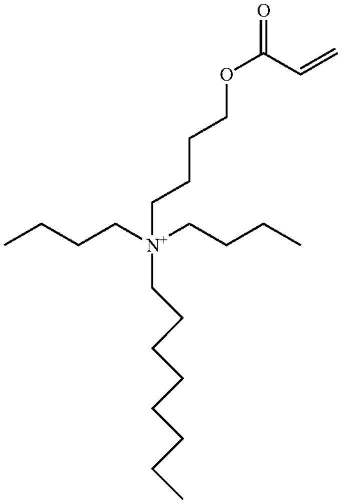
Monomer 10
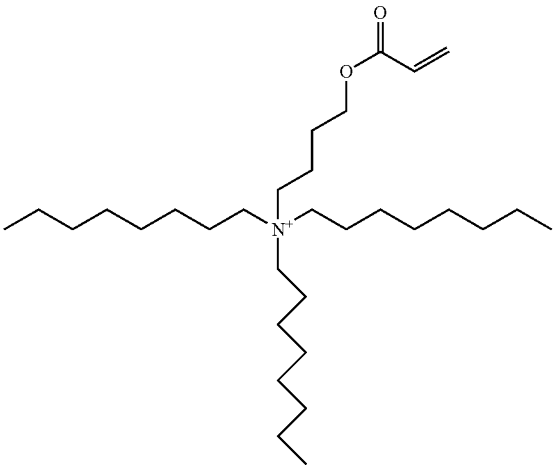
wherein each of the Monomers 1 to 10 is associated with an anion that does not impair the antibacterial strength of the composition.
19. The antibacterial composition of claim 1, wherein the anion is a halogen anion.
20. The antibacterial composition of claim 15, wherein the anion is a halogen anion.
* * * * *